United States Patent
Lewis et al.

(10) Patent No.: US 10,159,746 B2
(45) Date of Patent: Dec. 25, 2018

(54) CYCLODEXTRIN COMPLEXATION METHODS FOR FORMULATING PEPTIDE PROTEASOME INHIBITORS

(71) Applicant: Onyx Therapeutics, Inc., South San Francisco, CA (US)

(72) Inventors: Evan Lewis, Pacifica, CA (US); Peter Shwonek, San Francisco, CA (US); Sean Dalziel, San Francisco, CA (US); Mouhannad Jumaa, Foster City, CA (US)

(73) Assignee: Onyx Therapeutics, Inc., Thousand Oaks, CA (US)

( * ) Notice: Subject to any disclaimer, the term of this patent is extended or adjusted under 35 U.S.C. 154(b) by 0 days.

(21) Appl. No.: 14/399,582

(22) PCT Filed: May 8, 2013

(86) PCT No.: PCT/US2013/040127
§ 371 (c)(1),
(2) Date: Nov. 7, 2014

(87) PCT Pub. No.: WO2013/169897
PCT Pub. Date: Nov. 14, 2013

(65) Prior Publication Data
US 2015/0111838 A1    Apr. 23, 2015

Related U.S. Application Data

(60) Provisional application No. 61/777,475, filed on Mar. 12, 2013, provisional application No. 61/644,122, filed on May 8, 2012.

(51) Int. Cl.
*A61K 47/40* (2006.01)
*A61K 47/48* (2006.01)
(Continued)

(52) U.S. Cl.
CPC ........ *A61K 47/48969* (2013.01); *A61K 38/07* (2013.01); *A61K 47/6951* (2017.08); *B82Y 5/00* (2013.01)

(58) Field of Classification Search
None
See application file for complete search history.

(56) References Cited

U.S. PATENT DOCUMENTS 4,522,811 A    6/1985  Eppstein et al.
5,831,081 A    11/1998 Reuscher
(Continued)

FOREIGN PATENT DOCUMENTS

WO    WO-98/10779 A1    3/1998
WO    WO-2002/30455 A2    4/2002
(Continued)

OTHER PUBLICATIONS

Whalen et al. ('Specific effects of chloride ion in epoxide hydrolysis. The pH-dependence of the rates and mechanisms for the hydrolysis of indene oxide' Journal of the American Chemical Society v98(24) Nov. 24, 1976 pp. 7859-7861).*

(Continued)

*Primary Examiner* — Karlheinz R. Skowronek
*Assistant Examiner* — Ronald T Niebauer
(74) *Attorney, Agent, or Firm* — Marshall, Gerstein & Borun LLP

(57) ABSTRACT

This disclosure provides methods for formulating compositions comprising one or more peptide proteasome inhibitors and a cyclodextrin, particularly a substituted cyclodextrin. As well as cyclodextrin complexation methods of formulating a peptide proteasome inhibitor (e.g., a compound of formula (1)-(5) or a pharmaceutically acceptable salt thereof) with one or more cyclodextrins. Such methods substantially increase the solubility and stability of these proteasome inhibitors and facilitate both their manufacture and administration. For example, homogenous solutions of a compound of formula (5) (carfilzomib) can be obtained at a pharmaceutically useful pH (e.g., about 3.5) and at higher concentrations (e.g., about 5 mg/mL) than could be obtained without one or more cyclodextrins and the processes of complexation between the compound and one or more cyclodextrins provided herein.

(1)

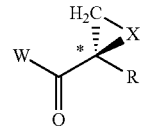

(2)

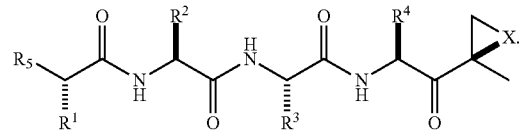

(3)

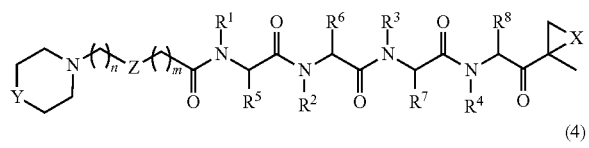

(4)

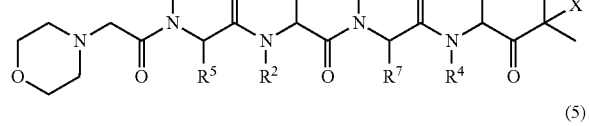

(5)

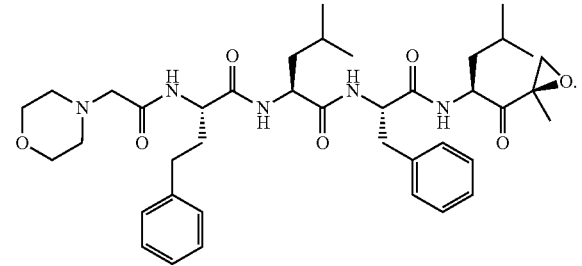

30 Claims, 8 Drawing Sheets
Specification includes a Sequence Listing.

(51) Int. Cl.
 *B82Y 5/00* (2011.01)
 *A61K 38/07* (2006.01)
 *A61K 47/69* (2017.01)

(56) References Cited

U.S. PATENT DOCUMENTS

| | | | |
|---|---|---|---|
| 6,153,746 | A | 11/2000 | Shah et al. |
| 6,471,996 | B1 | 10/2002 | Sokoll et al. |
| 6,472,375 | B1 | 10/2002 | Hoon et al. |
| 6,632,803 | B1 | 10/2003 | Harding |
| 6,831,099 | B1 | 12/2004 | Crews et al. |
| 7,232,818 | B2 | 6/2007 | Smyth et al. |
| 7,417,042 | B2 | 8/2008 | Smyth et al. |
| 7,491,704 | B2 | 2/2009 | Smyth et al. |
| 7,635,773 | B2 | 12/2009 | Antle |
| 7,737,112 | B2 | 6/2010 | Lewis et al. |
| 8,129,346 | B2 | 3/2012 | Smyth et al. |
| 8,207,125 | B2 | 6/2012 | Smyth et al. |
| 8,207,126 | B2 | 6/2012 | Smyth et al. |
| 8,207,127 | B2 | 6/2012 | Smyth et al. |
| 8,207,297 | B2 | 6/2012 | Smyth et al. |
| 9,493,582 | B2 | 11/2016 | Antle et al. |
| 9,511,109 | B2 | 12/2016 | Kirk et al. |
| 2004/0106539 | A1 | 6/2004 | Schubert et al. |
| 2009/0105156 | A1 | 4/2009 | Phiasivongsa et al. |
| 2011/0236428 | A1 | 9/2011 | Kirk et al. |
| 2015/0045311 | A1 | 2/2015 | Antle et al. |

FOREIGN PATENT DOCUMENTS

| | | |
|---|---|---|
| WO | WO-2005/105827 A2 | 11/2005 |
| WO | WO-2006/063154 A1 | 6/2006 |
| WO | WO-2013/130666 A1 | 9/2013 |

OTHER PUBLICATIONS

Definition of e. g. (retrieved from https://www.merriam-webster.com/dictionary/e.g. on Feb. 6, 2017, 13 pages).*
Gulder et al. ('Salinosporamide Natural Products: Potent 20 S Proteasome Inhibitors as Promising Cancer Chemotherapeutics' Angew. Chem. Int. Ed. V29 2010 pp. 9346-9367) (Year: 2010).*
Dalziel et al., A model for the approach to solubility equilibrium in crystallizing and dissolving systems, Dev. Chem. Eng. Mineral Process, 10(5-6):521-37 (2002).
Messner et al., Self-assembled cyclodextrin aggregates and nanoparticles, Int. J. Pharm., 387(1-2):199-208 (2010).
Adams, The proteasome: a suitable antineoplastic target, Nat. Rev. Cancer, 4(5):349-60 (2004).
Berge et al., Pharmaceutical salts, J. Pharm. Sci., 66(1):1-19 (1977).
Braun et al., Targeting NF-kappaB in hematologic malignancies, Cell Death Differ., 13(5):748-58 (2006).
Chapatte et al., Processing of tumor-associated antigen by the proteasomes of dendritic cells controls in vivo T-cell responses, Cancer Res., 66(10):5461-8 (2006).
Ciechanover, The ubiquitin-proteasome proteolytic pathway, Cell, 79(1):13-21 (1994).
Cilloni et al., Nuclear factor gammaBeta as a target for new drug development in myeloid malignancies, Haematologica, 92:1124-229 (2007).
Cohen, AIDS Mood Upbeat—for a Change, Science, 267:959-60 (1995).
Collins, Endothelial nuclear factor-kappa B and the initiation of the atherosclerotic lesion, Lab. Invest., 68(5):499-508 (1993).
Garrett et al., Selective inhibitors of the osteoblast proteasome stimulate bone formation in vivo and in vitro, J. Clin. Invest., 111(11):1771-82 (2003).
Gonzalez et al., Proteasome function is required for encystation of Entamoeba invadens, Arch. Med. Res., 28 Spec No. 139-40 (1997).
Hamajima et al., Intranasal administration of HIV-DNA vaccine formulated with a polymer, carboxymethylcellulose, augments mucosal antibody production and cell-mediated immune response, Clin. Immunol. Immunopathol., 88(2):205-10 (1998).
Hardy, The secret life of the hair follicle, Trends Genet., 8(2):55-61 (1992).
Harris et al., Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts, J. Bone Miner. Res., 9(6):855-63 (1994).
International Preliminary Report on Patentability for International Application No. PCT/US2013/040127, dated Nov. 11, 2014.
International Search Report and Written Opinion for International Application No. PCT/US2013/040127, dated Oct. 22, 2013.
Kojima et al., Two-way cleavage of beta-amyloid protein precursor by multicatalytic proteinase, FEBS Lett., 304(1):57-60 (1992).
Kumatori et al., Abnormally high expression of proteasomes in human leukemic cells, Proc. Natl. Acad. Sci. USA, 87(18):7071-5 (1990).
Palombella et al., The ubiquitin-proteasome pathway is required for processing the NF-kappa B1 precursor protein and the activation of NF-kappa B, Cell, 78(5):773-85 (1994).
Paugam et al., Characterization and role of protozoan parasite proteasomes, Trends Parasitol., 19(2):55-9 (2003).
Qureshi et al., The proteasome as a lipopolysaccharide-binding protein in macrophages: differential effects of proteasome inhibition on lipopolysaccharide-induced signaling events, J. Immunol., 171(3):1515-25 (2003).
Rolfe et al., The ubiquitin-mediated proteolytic pathway as a therapeutic area, J. Mol. Med. (Berl.), 75(1):5-17 (1997).
Simsek et al., Hepatitis B virus large and middle glycoproteins are degraded by a proteasome pathway in glucosidase-inhibited cells but not in cells with functional glucosidase enzyme, J. Virol., 79(20):12914-20 (2005).
Szalay et al., Ongoing coxsackievirus myocarditis is associated with increased formation and activity of myocardial immunoproteasomes, Am. J. Pathol., 168(5):1542-52 (2006).
Traenckner et al., A proteasome inhibitor prevents activation of NF-kappa B and stabilizes a newly phosphorylated form of I kappa B-alpha that is still bound to NF-kappa B, EMBO J., 13(22):5433-41 (1994).
Yu et al., The ubiquitin-proteasome system facilitates the transfer of murine coronavirus from endosome to cytoplasm during virus entry, J. Virol., 79(1):644-8 (2005).
Elofsson et al., Towards subunit-specific proteasome inhibitors: Synthesis and evaluation of peptide α'β'-epoxyketones. *Chem. Biol.* 6(11): 811-22 (1999).
Loftsson et al., Pharmaceutical applications of cyclodextrins. 1. Drug solubilization and stabilization. *J. Pharmaceut. Sci.* 85(10): 1017-25 (1996).
Myung et al., The ubiquitin-proteasome pathway and proteasome inhibitors. *Med. Res. Rev.* 21(4): 245-73 (2001).
USFDA Guidance for Industry Process Validation: General Principles and Practices, Published in Jan. 2011 Current Good Manufacturing Practices (CGMP).

* cited by examiner

Molar solubilized carfilzomib versus complexation indexed free cyclodextrin

CYCLODEXTRIN COMPLEXATION METHODS FOR FORMULATING PEPTIDE PROTEASOME INHIBITORS

CROSS REFERENCE TO RELATED APPLICATIONS

This application claims the benefit of U.S. Provisional Application No. 61/644,122, filed on May 8, 2012 and U.S. Provisional Application No. 61/777,475, filed on Mar. 12, 2013, each of which is incorporated herein by reference in its entirety.

INCORPORATION BY REFERENCE OF MATERIALS SUBMITTED ELECTRONICALLY

This application contains, as a separate part of disclosure, a Sequence Listing in computer-readable form (filename: 40073_SeqListing.txt; 989 byte—ASCII text file; created Dec. 16, 2015) which is incorporated by reference in its entirety.

TECHNICAL FIELD

This disclosure provides cyclodextrin complexation methods for formulating compositions comprising one or more peptide proteasome inhibitors and a cyclodextrin, or a mixture of cyclodextrins, particularly a substituted cyclodextrin(s). Such methods substantially increase the solubility and stability of these proteasome inhibitors and facilitate both their manufacture and administration.

BACKGROUND

The proteasome has been validated as a therapeutic target, as demonstrated by the FDA approval of bortezomib, a boronic acid proteasome inhibitor, for the treatment of various cancer indications, including multiple myeloma. However, other more highly proteasome-specific inhibitors that could have fewer toxic side effects have recently been described. These compounds include peptide epoxy ketones such as epoxomicin, described in U.S. Pat. No. 6,831,099, the contents of which are hereby incorporated by reference, and those described in U.S. Pat. No. 7,232,818, the contents of which are hereby incorporated by reference. However, the low aqueous solubility of some of these compounds makes it difficult to formulate compositions at sufficiently high concentration to enable practical administration with desired antineoplastic or other pharmacological effects. Thus, additional methods of formulating peptide epoxy ketones are needed.

SUMMARY

Provided herein are cyclodextrin complexation methods of formulating a peptide proteasome inhibitor (e.g., a compound of formula (1)-(5) or a pharmaceutically acceptable salt thereof) with one or more cyclodextrins. Many peptide proteasome inhibitors have been shown to have low solubility in water. This low solubility can be overcome through complexation of the compound with one or more cyclodextrins using the methods provided herein. For example, homogenous solutions of a compound of formula (5) (carfilzomib) can be obtained at a pharmaceutically useful pH (e.g., about 3.5) and at higher concentrations (e.g., about 5 mg/mL) than could be obtained without one or more cyclodextrins and the processes of complexation between the compound and one or more cyclodextrins provided herein. In addition to increasing the solubility of a peptide proteasome inhibitor in solution, the formulations prepared by the methods provided herein result in pharmaceutical solutions having surprising stability. The stability of a complexed inhibitor is reflected in the lack of precipitation from the homogeneous complexed inhibitor solution over extended periods of time and thermal stresses. For example, the complexed inhibitor can remain soluble for periods of time and under thermal stresses exceeding those typical for practical use of aseptically manufactured injectable pharmaceutical products. Although the high concentrations achieved by the processing methods provided herein may not be expected to be thermodynamically stable, the physical stability of the solutions have been shown to be unaffected by storage temperature (e.g., the solutions can be stable from −20° C. to 25° C.), freeze thaw cycling, and lyophilization and reconstitution. The stability of the supersaturated solutions of complexed peptide proteasome inhibitor and one or more cyclodextrins is sufficient to tolerate adjustments to pH following complexation without precipitation. For example, performing complexation in the pH range 2.5-3, then titrating the pH with sodium hydroxide solution to pH 3.5. This solution physical stability allows for use of the complexed material in a pH range acceptable for injection and other pharmaceutical purposes, as well exhibiting stability in a pH range where suitable chemical stability and shelf life is obtained. Accordingly, the pharmaceutical compositions prepared by the methods provided herein can be supersaturated solutions that do not precipitate or decrease in concentration to a significant extent during their use in any number of medical applications (e.g., a bulk solution during sterile product manufacture may not precipitate for several days post sterile filtration while being held in a vial filling sterile hold tank. Likewise, final reconstituted pharmaceutical compositions may be stable for a range of hours to days facilitating their use as medicinal agents).

In addition to producing stable, highly concentrated solutions of a peptide proteasome inhibitor, the formulations prepared by the complexation methods provided herein can be achieved without the chemical degradation and stability limitations of other methods of formulation. For example, the methods provided herein avoid the use of strong acids (e.g., HCl) to lower the pH during complexation. Although decreasing the pH of the formulation to a value less than 2 can facilitate the dissolution of the peptide proteasome inhibitor and produce a homogenous solution prior to complexation, the acidity of the solution can result in degradation of the peptide proteasome inhibitor. For example, in the case of the peptide proteasome inhibitor carfilzomib, use of a strong acid such as HCl can result in hydrolysis of the pharmacological epoxide, and through nucleophilic attack with chloride ions, result in formation of a chlorohydrin adduct as a degradant (CDP):

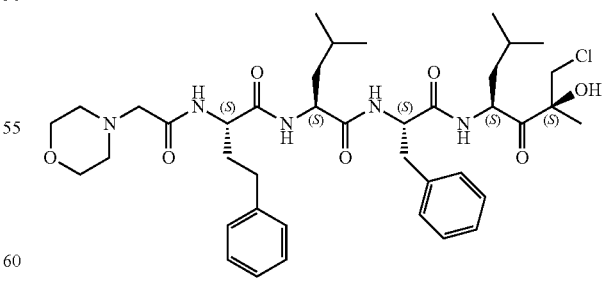

Based on its structure, this degradant is classified as an alkylator, which is a class of compound considered by the FDA to be a potentially genotoxic impurity. Importantly, from a regulated product safety standpoint, using the methods provided herein avoids such strong acids and therefore degradation reactions of the peptide proteasome inhibitor to such compounds can be significantly reduced and, in some cases, may even be eliminated.

In one aspect, methods for preparing a pharmaceutical composition are featured, which include:
(i) providing a first combination that includes:
(a) one (or more) peptide proteasome inhibitors (e.g., a compound of formula (1)-(5) or a pharmaceutically acceptable salt thereof);
(b) one or more cyclodextrins ("CDs"); and
(c) water;
wherein the first combination is heterogeneous and the compound or salt has a low solubility in the first combination; and
(ii) contacting the first combination with an acid to form a second combination, wherein the compound is more soluble in the second combination than in the first combination.

In another aspect, methods for preparing a pharmaceutical composition are featured, which include:
(i) providing a first combination that includes:
(a) a compound:

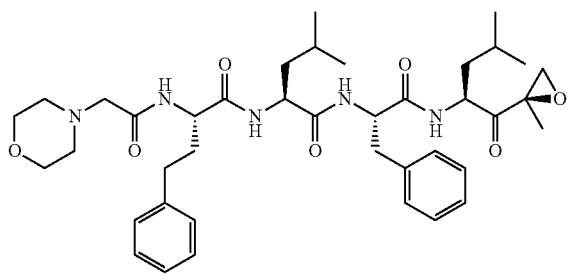 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof;
(b) one or more cyclodextrins ("CDs"); and
(c) water;
wherein the first combination is heterogeneous and the compound or salt has a low solubility in the first combination; and
(ii) contacting the first combination with an acid to form a second combination, wherein the compound is more soluble in the second combination than in the first combination.

In a further aspect, methods for preparing a pharmaceutical composition are featured, which include:
(i) providing a first combination that includes:
(a) a compound:

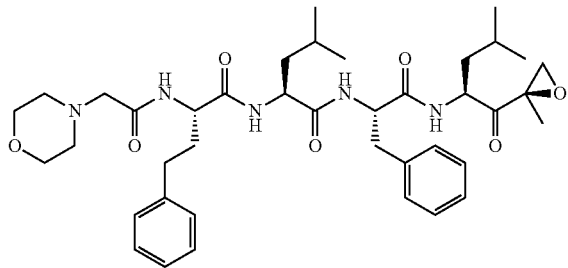 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof;
(b) SBECD; and
(c) water for injection;
wherein the first combination is heterogeneous and the compound or salt has a low solubility in the first combination; and (ii) contacting the first combination with an aqueous solution of citric acid to form a second combination, wherein the compound is more soluble in the second combination than in the first combination.

In one aspect, pharmaceutical compositions are featured, which are prepared by any one of the methods described herein.

In one aspect, methods for treating cancer (e.g., multiple myeloma, e.g., multiple myeloma that is relapsed and/or refractory) in a patient are featured, which include administering to the patient a therapeutically effective amount of a pharmaceutical composition prepared by any one of the methods described herein.

In another aspect, methods for treating autoimmune disease in a patient are featured, which include administering to the patient a therapeutically effective amount of a pharmaceutical composition prepared by any one of the methods described herein.

In another aspect, methods for treating graft or transplant-related condition in a patient are featured, which include administering to the patient a therapeutically effective amount of a pharmaceutical composition prepared by any one of the methods described herein.

In another aspect, methods for treating neurodegenerative disease in a patient are featured, which include administering to the patient a therapeutically effective amount of a pharmaceutical composition prepared by any one of the methods described herein.

In another aspect, methods for treating fibrotic-associated condition in a patient are featured, which include administering to the patient a therapeutically effective amount of a pharmaceutical composition prepared by any one of the methods described herein.

In another aspect, methods for treating fibrotic-associated condition in a patient are featured, which include administering to the patient a therapeutically effective amount of a pharmaceutical composition prepared by any one of the methods described herein.

In another aspect, methods for treating ischemic-related condition in a patient are featured, which include administering to the patient a therapeutically effective amount of a pharmaceutical composition prepared by any one of the methods described herein.

In another aspect, methods for treating an infection in a patient are featured, which include administering to the patient a therapeutically effective amount of a pharmaceutical composition prepared by any one of the methods described herein.

In another aspect, methods for treating an infection in a patient are featured, which include administering to the patient a therapeutically effective amount of a pharmaceutical composition prepared by any one of the methods described herein.

In another aspect, methods for treating disease associated with bone loss in a patient are featured, which include administering to the patient a therapeutically effective amount of a pharmaceutical composition prepared by any one of the methods described herein.

In another aspect, methods for treating an infection in a patient are featured, which include administering to the patient a therapeutically effective amount of a pharmaceutical composition prepared by any one of the methods described herein.

Embodiments can include one or more of the following features.

The first combination does not include appreciable amounts of any organic solvent(s). In some embodiments, the first combination does not include any amount or kind of organic solvent(s) described in U.S. Pat. No. 7,232,818 and/or U.S. Pat. No. 7,417,042 and/or U.S. Pat. No. 7,737,112 and/or US-2009-0105156 and/or US-2011-0236428, each of which is incorporated herein by reference. In some embodiments, the first combination is free of any organic solvent(s) (e.g., contains less than 5%, less than 4%, less than 3%, less than 2%, less than 1% (w/w or w/v) of any organic solvent(s)). In some embodiments, the first combination is substantially free of any organic solvent(s) (e.g., contains less than 0.5%, less than 0.2, less than 0.1, less than 0.05% (w/w or w/v) of any organic solvent(s)). In certain embodiments, the first combination does not include a detectable amount of any organic solvent(s).

The first combination does not include appreciable amounts of any buffer(s). In some embodiments, the first combination does not include any amount or kind of any buffer(s) described in U.S. Pat. No. 7,232,818 and/or U.S. Pat. No. 7,417,042 and/or U.S. Pat. No. 7,737,112 and/or US-2009-0105156 and/or US-2011-0236428, each of which is incorporated herein by reference. In some embodiments, the first combination is free of any buffer(s) (e.g., contains less than 5%, less than 4%, less than 3%, less than 2%, less than 1% (w/w or w/v) of any buffer(s)). In some embodiments, the first combination is substantially free of any buffer(s) (e.g., contains less than 0.5%, less than 0.2, less than 0.1, less than 0.05% (w/w or w/v) of any buffer(s)). In some embodiments, the first combination does not include a detectable amount of any buffer(s).

The second combination includes a complex of the compound and the one or more cyclodextrins.

The acid is added in the form of an aqueous solution.

At least one of the one or more cyclodextrins is HPBCD or SBECD (e.g., SBECD).

The inventors have discovered that it can be advantageous to minimize the amount of chloride ion (or other nucleophilic anions) in the methods and pharmaceutical compositions described herein.

In some embodiments, at least one of the one or more cyclodextrins (added to the first combination) is a low chloride cyclodextrin. As used herein, a "low chloride cyclodextrin" refers to a chloride-containing cyclodextrin having less than or equal to 0.05% w/w sodium chloride, or if a chloride source(s) other than (or in addition to) sodium chloride is/are present, a "low chloride cyclodextrin" refers to a chloride-containing cyclodextrin having a chloride ion content that is less than or equal to the amount of chloride that would be present in a cyclodextrin having 0.05% w/w sodium chloride. In some embodiments, the low chloride cyclodextrin is a low chloride SBECD. The determination of chloride concentration can be determined by a variety of methods known in the art (e.g., for commercially obtained cyclodextrans from the manufacturer's product specification, e.g., by gravimetric techniques, e.g., by potentiometric techniques).

In some embodiments, at least one of the one or more cyclodextrins (added to the first combination) does not include a detectable amount of chloride ion.

In some embodiments, the amount of chloride ion present (e.g., the mole ratio of chloride ion to compound) is sufficiently low so as to provide a shelf life of 2 years when stored at 2-8 degrees C. In certain embodiments, chloride ion is present, and the amount of chloride ion present is sufficiently low so as to provide a shelf life of 2 years when stored at 2-8 degrees C.

In some embodiments, the mole ratio of chloride ion to compound in the first combination is not more than 2.0. In certain embodiments, at least some chloride ion is present (i.e., the mole ratio of chloride ion to compound in the first combination is other than 0, but less than 2.0).

In some embodiments, the mole ratio of chloride ion to compound in the first combination is not more than 1.5. In certain embodiments, at least some chloride ion is present (i.e., the mole ratio of chloride ion to compound in the first combination is other than 0, but less than 1.5).

In some embodiments, the mole ratio of chloride ion to compound in the first combination is not more than 1.2. In certain embodiments, at least some chloride ion is present (i.e., the mole ratio of chloride ion to compound in the first combination is other than 0, but less than 1.2).

In some embodiments, the mole ratio of chloride ion to compound in the first combination is not more than 1.0. In certain embodiments, at least some chloride ion is present (i.e., the mole ratio of chloride ion to compound in the first combination is other than 0, but less than 1.0).

In some embodiments, the mole ratio of chloride ion to compound in the first combination is not more than 0.9. In certain embodiments, at least some chloride ion is present (i.e., the mole ratio of chloride ion to compound in the first combination is other than 0, but less than 0.9).

In some embodiments, the mole ratio of chloride ion to compound in the first combination is not more than 0.8. In certain embodiments, at least some chloride ion is present (i.e., the mole ratio of chloride ion to compound in the first combination is other than 0, but less than 0.8).

In some embodiments, the mole ratio of chloride ion to compound in the first combination is not more than 0.7. In certain embodiments, at least some chloride ion is present (i.e., the mole ratio of chloride ion to compound in the first combination is other than 0, but less than 0.7).

In some embodiments, the mole ratio of chloride ion to compound in the first combination is not more than 0.6. In certain embodiments, at least some chloride ion is present (i.e., the mole ratio of chloride ion to compound in the first combination is other than 0, but less than 0.6).

In some embodiments, the mole ratio of chloride ion to compound in the first combination is not more than 0.5. In certain embodiments, at least some chloride ion is present (i.e., the mole ratio of chloride ion to compound in the first combination is other than 0, but less than 0.5).

In some embodiments, the mole ratio of chloride ion to compound in the first combination is not more than 0.4. In certain embodiments, at least some chloride ion is present (i.e., the mole ratio of chloride ion to compound in the first combination is other than 0, but less than 0.4).

In some embodiments, the mole ratio of chloride ion to compound in the first combination is not more than 0.3. In certain embodiments, at least some chloride ion is present (i.e., the mole ratio of chloride ion to compound in the first combination is other than 0, but less than 0.3).

In some embodiments, the mole ratio of chloride ion to compound in the first combination is not more than 0.2. In certain embodiments, at least some chloride ion is present (i.e., the mole ratio of chloride ion to compound in the first combination is other than 0, but less than 0.2).

In some embodiments, the mole ratio of chloride ion to compound in the first combination is not more than 0.1. In certain embodiments, at least some chloride ion is present (i.e., the mole ratio of chloride ion to compound in the first combination is other than 0, but less than 0.1).

In some embodiments, the mole ratio of chloride ion to compound in the first combination is from 0.2 to 1.2 (e.g., 0.3 to 1.2, e.g., 0.2 to 0.4, e.g., 0.3 to 0.4, e.g., 0.32).

In embodiments, the mole ratios of chloride ion to compound described herein can also be present in the second and/or third combinations.

In one aspect, pharmaceutical compositions are featured, which are prepared by any one of the methods described herein and have a mole ratio of chloride ion to compound that is not more than 2.0. In certain embodiments, at least some chloride ion is present (i.e., the mole ratio of chloride ion to compound in the pharmaceutical compositions is other than 0, but less than 2.0).

In some embodiments, the mole ratio of chloride ion to compound in the pharmaceutical compositions is not more than 1.5. In certain embodiments, at least some chloride ion is present (i.e., the mole ratio of chloride ion to compound in the pharmaceutical compositions is other than 0, but less than 1.5).

In some embodiments, the mole ratio of chloride ion to compound in the pharmaceutical compositions is not more than 1.2. In certain embodiments, at least some chloride ion is present (i.e., the mole ratio of chloride ion to compound in the pharmaceutical compositions is other than 0, but less than 1.2).

In some embodiments, the mole ratio of chloride ion to compound in the pharmaceutical compositions is not more than 1.0. In certain embodiments, at least some chloride ion is present (i.e., the mole ratio of chloride ion to compound in the pharmaceutical compositions is other than 0, but less than 1.0).

In some embodiments, the mole ratio of chloride ion to compound in the pharmaceutical compositions is not more than 0.9. In certain embodiments, at least some chloride ion is present (i.e., the mole ratio of chloride ion to compound in the pharmaceutical compositions is other than 0, but less than 0.9).

In some embodiments, the mole ratio of chloride ion to compound in the pharmaceutical compositions is not more than 0.8. In certain embodiments, at least some chloride ion is present (i.e., the mole ratio of chloride ion to compound in the pharmaceutical compositions is other than 0, but less than 0.8).

In some embodiments, the mole ratio of chloride ion to compound in the pharmaceutical compositions is not more than 0.7. In certain embodiments, at least some chloride ion is present (i.e., the mole ratio of chloride ion to compound in the pharmaceutical compositions is other than 0, but less than 0.7).

In some embodiments, the mole ratio of chloride ion to compound in the pharmaceutical compositions is not more than 0.6. In certain embodiments, at least some chloride ion is present (i.e., the mole ratio of chloride ion to compound in the pharmaceutical compositions is other than 0, but less than 0.6).

In some embodiments, the mole ratio of chloride ion to compound in the pharmaceutical compositions is not more than 0.5. In certain embodiments, at least some chloride ion is present (i.e., the mole ratio of chloride ion to compound in the pharmaceutical compositions is other than 0, but less than 0.5).

In some embodiments, the mole ratio of chloride ion to compound in the pharmaceutical compositions is not more than 0.4. In certain embodiments, at least some chloride ion is present (i.e., the mole ratio of chloride ion to compound in the pharmaceutical compositions is other than 0, but less than 0.4).

In some embodiments, the mole ratio of chloride ion to compound in the pharmaceutical compositions is not more than 0.3. In certain embodiments, at least some chloride ion is present (i.e., the mole ratio of chloride ion to compound in the pharmaceutical compositions is other than 0, but less than 0.3).

In some embodiments, the mole ratio of chloride ion to compound in the pharmaceutical compositions is not more than 0.2. In certain embodiments, at least some chloride ion is present (i.e., the mole ratio of chloride ion to compound in the pharmaceutical compositions is other than 0, but less than 0.2).

In some embodiments, the mole ratio of chloride ion to compound in the pharmaceutical compositions is not more than 0.1. In certain embodiments, at least some chloride ion is present (i.e., the mole ratio of chloride ion to compound in the pharmaceutical compositions is other than 0, but less than 0.1).

In some embodiments, the pharmaceutical compositions do not include a detectable amount of chloride ion.

By way of example, the mole ratio of chloride ion to compound (e.g., in any one more of the following: the first combination, the second combination, the third combination, the pharmaceutical compositions prepared by the methods described herein) can be calculated as shown below using a dry powder vial of carfilzomib ("CFZ") as the basis for the calculation:

Vial content mass=3.212 g

CFZ mass=61.8 mg

Chloride max mass (at 0.03% w/w chloride ion) =0.0009636 g

Chloride max mole mass=$2.714 \times 10^{-5}$ (atomic mass Cl=35.5)

CFZ mole mass=$8.584 \times 10^{-5}$ (MW CFZ=719.9)

Mole ratio Cl/CFZ in solid state in a vial=0.32

This calculation can also be determined for the first combination using, e.g., the chloride content of the cyclodextran (and any other chloride ion source) and the mass of the compound that are added to make the first combination.

As the skilled artisan can appreciate, this ratio would be expected to the same in the precursor bulk solution used to fill the vial (pre-lyophilization) as well as when the contents of said dry powder vial are reconstituted in sterile water for patient administration.

Providing a first combination (step (i)) includes adding the compound to a solution of the one or more cyclodextrins and the water.

The compound is a crystalline solid. In embodiments, the crystalline form of the compound has an X-ray powder diffraction pattern comprising 2 to 8 characteristic peaks expressed in degrees 2θ at 6.10, 9.32, 10.10, 12.14, 13.94, 18.44, 20.38, and 23.30.

The method further includes mixing the first combination prior to contacting the first combination with an acid.

Steps (i) and (ii) are both performed in a single vessel.

The method further includes mixing the second combination for a time sufficient to achieve a homogeneous third combination.

The dissolved and complexed concentration of the compound in the third combination is from 1 mg/mL to 20 mg/mL.

The dissolved and complexed concentration of the compound in the third combination is from 4 to 8 mg/mL.

The pH of the third combination is from 2 to 4.

The method further includes filtering the third combination.

The method further comprises lyophilizing the third combination to provide a lyophilizate.

The method further comprises mixing the lyophilizate with a pharmaceutically acceptable carrier.

The pharmaceutically acceptable carrier comprises sterile water for injection. In embodiments, the pharmaceutically acceptable carrier further includes citric acid.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION

Figure 1:
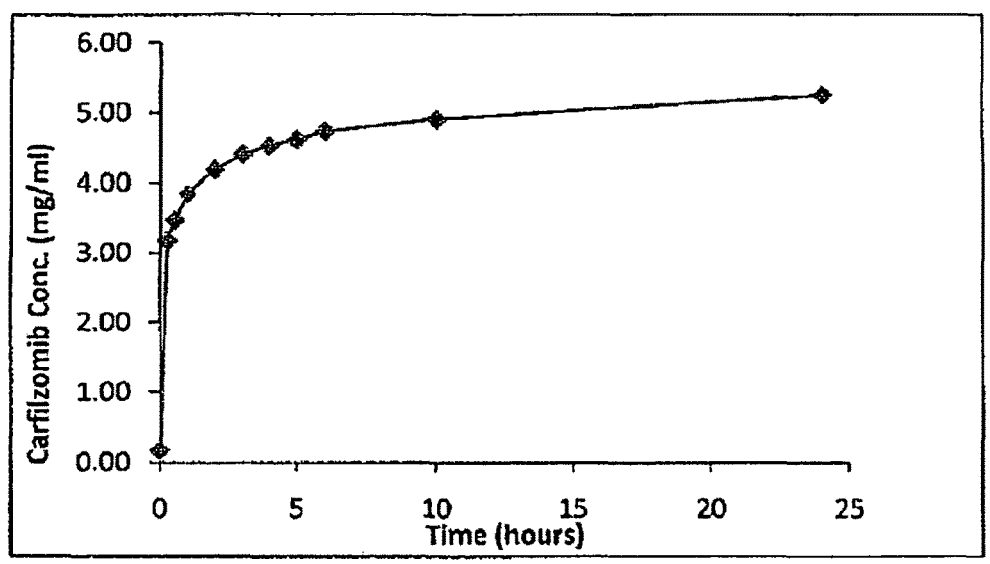
FIG. 1 is a line graph showing complexation of CFZ-API by SBECD over time.

Provided herein are cyclodextrin complexation methods of formulating a peptide proteasome inhibitor (e.g., a compound of formula (1)-(5) or a pharmaceutically acceptable salt thereof) with a cyclodextrin. Also provided herein are pharmaceutical compositions comprising a peptide proteasome inhibitor and a cyclodextrin, wherein the composition has a chloride ion as described anywhere herein (e.g., the composition is prepared using a low chloride cyclodextrin; e.g., the mole ratio of chloride ion to compound is 0.32). In some embodiments, formulations having low chloride ion content as described herein can result in decreased formation of undesired degradation products.

Definitions

The term "$C_{x-y}$alkyl" refers to substituted or unsubstituted saturated hydrocarbon groups, including straight-chain and branched-chain alkyl groups that contain from x to y carbons in the chain, including haloalkyl groups such as trifluoromethyl and 2,2,2-trifluoroethyl, etc. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

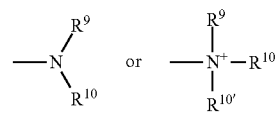

where $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In some embodiments, only one of $R^9$ or $R^{10}$ is a carbonyl, e.g., $R^9$, $R^{10}$, and the nitrogen together do not form an imide. In some embodiments, $R^9$ and $R^{10}$ (and optionally $R^{10'}$) each independently represent a hydrogen, an alkyl, an alkenyl, or —$(CH_2)_m$—$R^8$. In certain embodiments, an amino group is basic, meaning its protonated form has a pKa above 7.00.

The terms "amide" and "amido" are art-recognized as an amino-substituted carbonyl and includes a moiety that can be represented by the general formula:

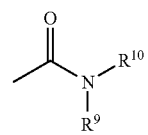

wherein $R^9$, $R^{10}$ are as defined above. In some embodiments, the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "buffer" is a substance which by its presence in solution increases the amount of acid or alkali that must be added to cause a unit change in pH. Thus, a buffer is a substance that assists in regulating the pH of a composition. Typically, a buffer is chosen based upon the desired pH and compatibility with other components of a composition. In general, a buffer has a pKa that is no more than 1 unit less than or greater than the desired pH of the composition (or that the composition will produce upon dissolution).

The term "water" as used herein refers to a liquid solution of H$_2$O having a pH of approximately 7.0.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formulae:

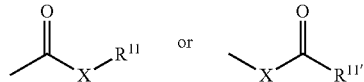

wherein X is a bond or represents an oxygen or a sulfur, and R$^{11}$ represents a hydrogen, an alkyl, an alkenyl, —(CH$_2$)$_m$—R$^8$ or a pharmaceutically acceptable salt, R$^{11'}$ represents a hydrogen, an alkyl, an alkenyl or —(CH$_2$)$_m$—R$^8$, where m and R$^8$ are as defined above. Where X is an oxygen and R$^{11}$ or R$^{11'}$ is not hydrogen, the formula represents an "ester". Where X is an oxygen, and R$^{11}$ is a hydrogen, the formula represents a "carboxylic acid".

The term "C$_{1-6}$heteroaralkyl", as used herein, refers to a C$_{1-6}$alkyl group substituted with a heteroaryl group.

The term "heteroaryl" includes substituted or unsubstituted aromatic 5- to 7-membered ring structures, for example, 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. For example, heteroatoms include nitrogen, oxygen, phosphorus, and sulfur.

The term "heterocyclyl" or "heterocyclic group" refers to substituted or unsubstituted non-aromatic 3- to 10-membered ring structures, for example, 3- to 7-membered rings, whose ring structures include one to four heteroatoms. The term "heterocyclyl" or "heterocyclic group" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "C$_{1-6}$hydroxyalkyl" refers to a C$_{1-6}$alkyl group substituted with a hydroxy group.

The term "thioether" refers to an alkyl group, as defined above, having a sulfur moiety attached thereto. In some embodiments, the "thioether" is represented by —S— alkyl. Representative thioether groups include methylthio, ethylthio, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

In some embodiments, the compounds provided herein, or salts thereof, are substantially isolated or purified. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds, or salt thereof. Methods for isolating compounds and their salts are routine in the art.

As used herein, the term "peptide" refers to a chain of amino acids that is about two to about ten amino acids in length.

As used herein, the term "natural" or "naturally occurring" amino acid refers to one of the twenty most common occurring amino acids. Natural amino acids are referred to by their standard one- or three-letter abbreviations.

The term "non-natural amino acid" or "non-natural" refers to any derivative or structural analogue of a natural amino acid including D forms, and β and γ amino acid derivatives. It is noted that certain amino acids, e.g., hydroxyproline, that are classified as a non-natural amino acid herein, may be found in nature within a certain organism or a particular protein. Non-limiting examples of non-natural amino acids include: β-Alanine (β-Ala), γ-Aminobutyric Acid (GABA), 2-Aminobutyric Acid (2-Abu), α,β-Dehydro-2-aminobutyric Acid (Δ-Abu), 1-Aminocyclopropane-1-carboxylic Acid (ACPC), Aminoisobutyric Acid (Aib), 2-Amino-thiazoline-4-carboxylic Acid, 5-Aminovaleric Acid (5-Ava), 6-Aminohexanoic Acid (6-Ahx), 8-Aminooctanoic Acid (8-Aoc), 11-Aminoundecanoic Acid (11-Aun), 12-Aminododecanoic Acid (12-Ado), 2-Aminobenzoic Acid (2-Abz), 3-Aminobenzoic Acid (3-Abz), 4-Aminobenzoic Acid (4-Abz), 4-Amino-3-hydroxy-6-methylheptanoic Acid (Statine, Sta), Aminooxyacetic Acid (Aoa), 2-Aminotetraline-2-carboxylic Acid (Atc), 4-Amino-5-cyclohexyl-3-hydroxypentanoic Acid (ACHPA), para-Aminophenylalanine (4-NH$_2$-Phe), Biphenylalanine (Bip), para-Bromophenylalanine (4-Br-Phe), ortho-Chlorophenylalanine (2-Cl-Phe), meta-Chlorophenylalanine (3-Cl-Phe), para-Chlorophenylalanine (4-Cl-Phe), meta-Chlorotyrosine (3-Cl-Tyr), para-Benzoylphenylalanine (Bpa), tert-Butylglycine (Tle), Cyclohexylalanine (Cha), Cyclohexylglycine (Chg), 2,3-Diaminopropionic Acid (Dpr), 2,4-Diaminobutyric Acid (Dbu), 3,4-Dichlorophenylalanine (3,4-Cl2-Phe), 3,4-Diflurorphenylalanine (3,4-F2-Phe), 3,5-Diiodotyrosine (3,5-12-Tyr), ortho-Fluorophenylalanine (2-F-Phe), meta-Fluorophenylalanine (3-F-Phe), para-Fluorophenylalanine (4-F-Phe), meta-fluorotyrosine (3-F-Tyr), Homoserine (Hse), Homophenylalanine (Hfe), Homotyrosine (Htyr), 5-Hydroxytryptophan (5-0H-Trp), Hydroxyproline (Hyp), para-Iodophenylalanine (4-1-Phe), 3-Iodotyrosine (3-I-Tyr), Indoline-2-carboxylic Acid (Idc), Isonipecotic Acid (Inp), meta-methyltyrosine (3-Me-Tyr), I-Naphthylalanine (1-Nal), 2 Naphthylalanine (2-Nal), para-Nitrophenylalanine (4-NO$_2$-Phe), 3-Nitrotyrosine (3-NO$_2$-Tyr), Norleucine (Nle), Norvaline (Nva), Omithine (Orn), ortho-Phosphotyrosine (H$_2$P0$_3$-Tyr), Octahydroindole-2-carboxylic Acid (Oic), Penicillamine (Pen), Pentafluorophenylalanine (F5-Phe), Phenylglycine (Phg), Pipecolic Acid (Pip), Propargylglycine (Pra), Pyroglutamic Acid (pGlu), Sarcosine (Sar), Tetrahydroisoquinoline-3-carboxylic Acid (Tic), and Thiazolidine-4-carboxylic Acid (Thioproline, Th). Stereochemistry of amino acids may be designated by preceding the name or abbreviation with the designation "D" or "d" or "L" or "1" as appropriate. Alternately, chiral centers may be represented with conventional (S)-, or (R)-designations. Additionally, αN-alkylated amino acids may be employed, as well as amino acids having amine-containing side chains (such as Lys and Orn) in which the amine has been acylated or alkylated. See, for example, "Peptides and Mimics, Design of Conformationally Constrained" by Hruby and Boteju, in Molecular Biology and Biotechnology: A Comprehensive Desk Reference, ed. Robert A. Meyers, VCH Publishers (1995), pp. 658-664, which is hereby incorporated by reference.

The term "complexation" as used herein refers to the formation of an intermolecular inclusion complex, or an intermolecular association, in solution and between one or more peptide proteasome inhibitors and one or more cyclodextrin molecules. The inclusion and or the association provides utility as a mechanism of substantially increasing the concentration of the inhibitor(s) that can be achieved in aqueous solution compared to aqueous phase dissolution in a similar pH range without the complexing agent (i.e., one or more cyclodextrin molecules). In some embodiments, the cyclodextrin (e.g., SBECD, e.g., from a low chloride:cyclodextrin source, e.g., a low chloride SBECD):inhibitor (e.g., carfilzomib) ratio is 1:1. In other embodiments, more than one cyclodextran (e.g., each independently selected from SBECD, a low chloride:cyclodextrin and a low chloride SBECD) can be complexed to a particular inhibitor (e.g., 2, 3, 4, 5, or 6; e.g., 2 or 3) cyclodextrans (e.g., each independently selected from SBECD, a low chloride:cyclodextrin and a low chloride SBECD) can be complexed to a particular inhibitor (e.g., carfilzomib). In some embodiments, the cyclodextrin (e.g., SBECD, e.g., from a low chloride:cyclodextrin source, e.g., a low chloride SBECD): inhibitor (e.g., carfilzomib) ratio is from 1-5:1 (e.g., 1-4:1; 1-3:1; 1-2:1; 2-5:1, 2-4:1, 2-3:1). Complexation ratios can be determined using, e.g., the methods described herein.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

As used herein, the term "inhibitor" is meant to describe a compound that blocks or reduces an activity of an enzyme or system of enzymes, receptors, or other pharmacological target (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

As used herein, "low solubility" refers to being sparingly soluble, slightly soluble, very slightly soluble, practically insoluble, or insoluble in, for example, water or another solution (e.g., a first combination); the terms "sparingly soluble, slightly soluble, very slightly soluble, practically insoluble, or insoluble" correspond in meaning to the United States Pharmacopeia (USP) general terms for approximate solubility expression. See, e.g., DeLuca and Boylan in *Pharmaceutical Dosage Forms: Parenteral Medications*, vol. I, Avis, K. E., Lackman, L. and Lieberman, H. A., eds; Marcel Dekkar: 1084, pages 141-142:

| USP term | Relative amount of solvent to dissolve 1 part of solute |
|---|---|
| sparingly soluble | 30-100 |
| Slightly soluble | 100-1,000 |
| very slightly soluble | 1,000-10,000 |
| practically insoluble, or insoluble | >10,000 |

"Heterogeneous" as used herein refers to a solution having a non-uniform (multiphase) composition. For example, a heterogeneous solution can include a suspension of solid particles in a liquid (e.g., a slurry).

"Homogeneous" as used herein refers to a solution that is consistent or uniform throughout its volume (single phase, observed as clear solution).

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

Compounds

Provided herein are methods for preparing formulations of peptide proteasome inhibitors that have low solubility characteristics in water. Peptide proteasome inhibitors comprise an epoxide- or aziridine-containing moiety, which contains groups proximate to the heteroatom-containing, three-membered rings, such that a ring-opening reaction of the heteroatom-containing three-membered ring is facilitated. Such groups include, for example, electron withdrawing groups such as a carbonyl. In some embodiments, a peptide proteasome inhibitor is a peptide epoxy proteasome inhibitor. As used herein, a "peptide epoxy proteasome inhibitor" comprises a ketone moiety having an epoxy group on one side of the ketone with a peptide on the other.

The peptide of a peptide proteasome inhibitor includes 2 to 10 amino acids. For example, the peptide can have 2 to 8 amino acids; 2 to 6 amino acids; 2 to 5 amino acids; 2 to 4 amino acids; 3 to 10 amino acids; 4 to 10 amino acids; 6 to 10 amino acids; 8 to 10 amino acids; 3 to 4 amino acids; 3 to 5 amino acids; and 4 to 6 amino acids. In some embodiments, the peptide has 3 or 4 amino acids.

In some embodiments, a peptide proteasome inhibitor is a compound of formula (1):

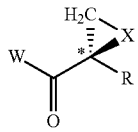

wherein:
X is oxygen, NH, or N($C_{1-6}$ alkyl);
W is a peptide comprising two to ten amino acids, wherein the amino acids can be natural, non-natural, or a combination thereof; and
R is a hydrogen atom or a $C_{1-4}$ alkyl group, which can be substituted with one or more of a hydroxy, halogen, amino, carboxy, carbonyl, thio, sulfide, ester, amide or ether functionality;
or a pharmaceutically acceptable salt thereof.

In some embodiments, X is configured to facilitate interaction with an N-terminal nucleophilic group in an Ntn hydrolase. For example, irreversible interactions of enzyme inhibitors with the β5/Pre2 subunit of 20S proteasome which lead to inhibition appear to be facilitated by the configuration illustrated above. In the case of other Ntn hydrolases, the opposite stereochemistry of the α-carbon of the peptide epoxides or peptide aziridines may be useful. In some embodiments, X is oxygen.

The stereochemistry of the α'-carbon (that carbon forming a part of the epoxide or aziridine ring) can be (R) or (S). Note that a compound may have a number of stereocenters having the indicated up-down (or β-α, where β as drawn herein is above the plane of the page) or (R)-(S) relationship (that is, it is not required that every stereocenter in the compound conform to the preferences stated). In some embodiments, the stereochemistry of the α' carbon is (R), that is, the X atom is β, or above the plane of the molecule, when drawn as in formula (1).

In the case of a compound of formula (1), the β' carbon is substituted with two hydrogen atoms. Regarding the stereochemistry, the chiral α' carbon is indicated with a star, and the Cahn-Ingold-Prelog rules for determining absolute stereochemistry are followed. These rules are described, for example, in Organic Chemistry, Fox and Whitesell; Jones and Bartlett Publishers, Boston, Mass. (1994); Section 5-6, pp 177-178, which section is hereby incorporated by reference. The stereochemistry of the α' carbon is (R) when the oxygen or nitrogen has the highest priority, the peptide-ketone group has second highest priority, and the —$CH_2$—X— group has third highest priority. If the relative priorities of the peptide-ketone, —$CH_2$—X—, and R groups change, the nominal stereochemistry can change, but the essential configuration of the groups can remain the same, for some embodiments. That is, referring to the general structure immediately above, the peptide-ketone is joined to the chiral α' carbon from the left, R is joined to the chiral α' carbon from the right, and the X atom(s) project(s) from the plane of the page. The nitrogen atom of an aziridine ring can also, in principle, be chiral, as discussed in March, Advanced Organic Chemistry, 4th Ed. (1992) Wiley-Interscience, New York, pp. 98-100, which pages are incorporated herein by reference.

W is a peptide comprising two to ten amino acids, wherein the amino acids can be natural, non-natural, or a combination thereof. For example, the peptide can have 2 to 8 amino acids; 2 to 6 amino acids; 2 to 5 amino acids; 2 to 4 amino acids; 3 to 10 amino acids; 4 to 10 amino acids; 6 to 10 amino acids; 8 to 10 amino acids; 3 to 4 amino acids; 3 to 5 amino acids; and 4 to 6 amino acids. In some embodiments, the peptide has 3 or 4 amino acids. In some embodiments useful for inhibiting chymotrypsin-like (CT-L) activity of the proteasome, between four and eight amino acids are present, and in some embodiments for CT-L inhibition, between four and six amino acids are present. In other embodiments useful for inhibiting the PGPH activity of the proteasome, between two and eight amino acids are present, and in some embodiments for PGPH inhibition, between three and six amino acids are present. The bond between W and the ketone moiety in the formula (1) can be made between either termini of the peptide. For example, in some embodiments, the ketone is bonded to carboxy terminus of the peptide. Alternatively, the ketone can be bonded to the amino terminus of the peptide. In some embodiments, the ketone can be bonded to a side chain of the peptide.

Examples of a compound of formula (1) can be found in U.S. Pat. No. 7,737,112, which is incorporated by reference in its entirety herein. In some embodiments, a compound of formula (1) has a low solubility in water.

A peptide proteasome inhibitor for inhibition of chymotrypsin-like (CT-L) activity of Ntn can include a peptide having at least four amino acids. In some CT-L inhibitor embodiments, the inhibitor has a peptide having at least four amino acids and an α',β'-epoxy ketone or α',β'-aziridine ketone moiety (tetrapeptide epoxy ketones or tetrapeptide aziridine ketones).

In some embodiments, a peptide proteasome inhibitor having low water solubility can be a compound of formula (II):

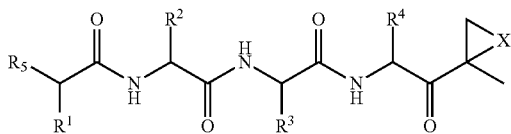

wherein:
each A is independently selected from C=O, C=S, and SO$_2$; or
A is optionally a covalent bond when adjacent to an occurrence of Z;
L in absent or is selected from C=O, C=S, and SO$_2$;
M is absent or is C$_{1-12}$alkyl;
Q is absent or is selected from O, NH, and N(C$_{1-6}$alkyl);
X is selected from O, NH, and N(C$_{1-6}$alkyl);
Y is absent or is selected from O, NH, N(C$_{1-6}$alkyl), S, SO, SO$_2$, CHOR$^{10}$, and CHCO$_2$R$^{10}$;
each Z is independently selected from O, S, NH, and N(C$_{1-6}$alkyl); or
Z is optionally a covalent bond when adjacent to an occurrence of A;
R$^1$, R$^2$, R$^3$, and R$^4$ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid (or a salt thereof), ester, thiol, or thioether substituents;
R$^5$ is N(R$^6$)LQR$^7$;
R$^6$ is selected from hydrogen, OH, and C$_{1-6}$alkyl;
R$^7$ is selected from hydrogen, C$_{1-6}$alkyl, C$_{1-6}$alkenyl, C$_{1-6}$alkynyl, aryl, C$_{1-6}$aralkyl, heteroaryl, C$_{1-6}$ heteroaralkyl, R$^8$ZAZ-C$_{1-8}$alkyl-, R$^{11}$Z—C$_{1-8}$alkyl-, (R$^8$O)(R$^9$O)P(=O)O—C$_{1-8}$alkyl-ZAZ-C$_{1-8}$alkyl-, R$^8$ZAZ-C$_{1-8}$alkyl-ZAZ-C$_{1-8}$alkyl-, heterocyclylMZAZ-C$_{1-8}$alkyl-, (R$^8$O)(R$^9$O)P(=O)O—C$_{1-8}$alkyl-, (R$^{10}$)$_2$N—C$_{1-12}$alkyl-, (R$^{10}$)$_3$N$^+$—C$_{1-12}$alkyl-, heterocyclylM-, carbocyclylM-, R$^{11}$SO$_2$C$_{1-8}$alkyl-, and R$^{11}$SO$_2$NH; or
R$^6$ and R$^7$ together are C$_{1-6}$alkyl-Y—C$_{1-6}$alkyl, C$_{1-6}$alkyl-ZAZ-C$_{1-6}$alkyl, ZAZ-C$_{1-6}$alkyl-ZAZ-C$_{1-6}$alkyl, ZAZ-C$_{1-6}$alkyl-ZAZ, or C$_{1-6}$alkyl-A, thereby forming a ring;
R$^8$ and R$^9$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, or R$^8$ and R$^9$ together are C$_{1-6}$alkyl, thereby forming a ring;
each R$^{10}$ is independently selected from hydrogen and C$_{1-6}$alkyl; and
R$^{11}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl,
provided that when R$^6$ is H or CH$_3$ and Q is absent, LR$^7$ is not hydrogen, unsubstituted C$_{1-6}$alkylC=O, a further chain of amino acids, t-butoxycarbonyl (Boc), benzoyl (Bz), fluoren-9-ylmethoxycarbonyl (Fmoc), triphenylmethyl (trityl), benzyloxycarbonyl (Cbz), trichloroethoxycarbonyl (Troc); or substituted or unsubstituted aryl or heteroaryl; and
in any occurrence of the sequence ZAZ, at least one member of the sequence must be other than a covalent bond;
or a pharmaceutically acceptable salt thereof.

In certain embodiments, when R$^6$ is H, L is C=O, and Q is absent, R$^7$ is not hydrogen, C$_{1-6}$alkyl, or substituted or unsubstituted aryl or heteroaryl. In certain embodiments, when R$^6$ is H and Q is absent, R$^7$ is not a protecting group such as those described in Greene, T. W. and Wuts, P. G. M., "Protective Groups in Organic Synthesis", John Wiley & Sons, 1999 or Kocienfski, P. J., "Protecting Groups", Georg Thieme Verlag, 1994.

In some embodiments, R$^1$, R$^2$, R$^3$, and R$^4$ are selected from C$_{1-6}$alkyl or C$_{1-6}$aralkyl. For example, R$^2$ and R$^4$ are C1-6alkyl and R$^1$ and R$^3$ are C1-6aralkyl. In the some embodiments, R$^2$ and R$^4$ are isobutyl, R$^1$ is 2-phenylethyl, and R$^3$ is phenylmethyl.

In some embodiments, L and Q are absent and R$^7$ is selected from C$_{1-6}$alkyl, C$_{1-6}$alkenyl, C$_{1-6}$alkynyl, C$_{1-6}$alkyl, and C$_{1-6}$heteroaralkyl. For example, R$^6$ is C$_{1-6}$alkyl and R$^7$ is selected from butyl, allyl, propargyl, phenylmethyl, 2-pyridyl, 3-pyridyl, and 4-pyridyl.

In some embodiments, L is SO$_2$, Q is absent, and R$^7$ is selected from C$_{1-6}$alkyl and aryl. For example, R$^7$ can be selected from methyl and phenyl.

In some embodiments, L is C=O and R$^7$ is selected from C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-R$^{11}$Z—C$_{1-8}$alkyl-, (R$^8$O)(R$^9$O)P(=O)O—C$_{1-8}$alkyl-, (R$^8$O)(R$^9$O)P(=O)O—C$_{1-8}$alkyl-ZAZ-C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ-C$_{1-8}$alkyl-, heterocyclylMZAZ-C$_{1-8}$alkyl-, (R$^{10}$)2N—C$_{1-8}$alkyl-, (R$^{10}$)3N+—C$_{1-8}$alkyl-, heterocyclyl-M carbocyclylM-, R$^{11}$SO2C$_{1-8}$alkyl-, and R$^{11}$SO2NH—, wherein each occurrence of Z and A is independently other than a covalent bond. In some embodiments, L is C=O, Q is absent, and R$^7$ is H.

In some embodiments, R$^6$ is C$_{1-6}$alkyl, R$^7$ is C$_{1-6}$alkyl, Q is absent, and L is C=O. In certain such embodiments, R$^7$ is ethyl, isopropyl, 2,2,2-trifluoroethyl, or 2-(methylsulfonyl)ethyl.

In some embodiments, L is C=O, Q is absent, and R$^7$ is C$_{1-6}$aralkyl. For example, R$^7$ can be selected from 2-phenylethyl, phenylmethyl, (4-methoxyphenyl)methyl, (4-chlorophenyl)methyl, and (4-fluorophenyl)methyl.

In some embodiments, L is C=O, Q is absent, R$^6$ is C$_{1-6}$alkyl, and R$^7$ is aryl. For example, R$^7$ can be a substituted or unsubstituted phenyl.

In some embodiments, L is C=O, Q is absent or O, n is 0 or 1, and R$^7$ is —(CH$_2$)$_n$carbocyclyl. For example, R$^7$ can be cyclopropyl or cyclohexyl.

In some embodiments, L and A are C=O, Q is absent, Z is O, n is an integer from 1 to 8 (e.g., 1), and R$^7$ is selected from R$^8$ZA-C$_{1-8}$alkyl-, R$^{11}$Z—C$_{1-8}$alkyl-, R$^8$ZA-C$_{1-8}$alkyl-ZAZ-C$_{1-8}$alkyl-, (R$^8$O)(R$^9$O)P(=O)O—C$_{1-8}$alkyl-ZAZ-C$_{1-8}$alkyl-, (R$^8$O)(R$^9$O)P(=O)O—C$_{1-8}$alkyl-Z—C$_{1-8}$alkyl-, and heterocyclylMZAZ-C$_{1-8}$alkyl-, wherein each occurrence of A is independently other than a covalent bond. For example, R$^7$ can be heterocyclylMZAZ-C$_{1-8}$alkyl- where heterocyclyl is a substituted or unsubstituted oxodioxolenyl or N(R$^{12}$)(R$^{13}$), wherein R$^{12}$ and R$^{13}$ together are C$_{1-6}$alkyl-Y—C$_{1-6}$alkyl, such as C$_{1-3}$alkyl-Y—C$_{1-3}$alkyl, thereby forming a ring.

In some embodiments, L is C=O, Q is absent, n is an integer from 1 to 8, and R$^7$ is selected from (R$^8$O)(R$^9$O)P(=O)O—C$_{1-8}$alkyl-, (R$^{10}$)$_2$NC$_{1-8}$alkyl, (R$^{10}$)$_3$N$^+$(CH$_2$)n-, and heterocyclyl-M-. In certain such embodiments, R$^7$ is —C$_{1-8}$alkylN(R$^{10}$)$_2$ or —C$_{1-8}$alkylN$^+$(R$^{10}$)$_3$, where R$^{10}$ is C$_{1-6}$alkyl. For example, R$^7$ is heterocyclylM-, where heterocyclyl is selected from morpholino, piperidino, piperazino, and pyrrolidino.

In some embodiments, L is C=O, R$^6$ is C$_{1-6}$alkyl, Q is selected from O and NH and R$^7$ is selected from C$_{1-6}$alkyl, cycloalkyl-M, C$_{1-6}$aralkyl, and C$_{1-6}$heteroaralkyl. In some embodiments, L is C=O, R$^6$ is C$_{1-6}$alkyl, Q is selected from O and NH, and R$^7$ is C$_{1-6}$alkyl, where C$_{1-6}$alkyl is selected from methyl, ethyl, and isopropyl. In some embodiments, L is C=O, $R^6$ is $C_{1-6}$alkyl, Q is selected from O and NH and $R^7$ is $C_{1-6}$alkyl, where aralkyl is phenylmethyl. In some embodiments, L is C=O, $R^6$ is $C_{1-6}$alkyl, Q is selected from O and NH, and $R^7$ is $C_{1-6}$heteroaralkyl, where heteroaralkyl is (4-pyridyl)methyl.

In some embodiments, L is absent or is C=O, and $R^6$ and $R^7$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In some embodiments, L is C=O, Q and Y are absent, and $R^6$ and $R^7$ together are $C_{1-3}$alkyl-Y—$C_{1-3}$alkyl. In some embodiments, L and Q are absent, and $R^6$ and $R^7$ together are $C_{1-3}$alkyl-Y—$C_{1-3}$alkyl. In some embodiments, L is C=O, Q is absent, Y is selected from NH and N—$C_{1-6}$alkyl, and $R^6$ and $R^7$ together are $C_{1-3}$alkyl-Y—$C_{1-3}$alkyl. In some embodiments, L is C=O, Y is absent, and $R^6$ and $R^7$ together are $C_{1-3}$alkyl-Y—$C_{1-3}$alkyl. In some embodiments, L and A are C=O, and $R^6$ and $R^7$ together are $C_{1-2}$alkyl-ZA-$C_{1-2}$alkyl. In some embodiments, L and A are C=O and $R^6$ and $R^7$ together are $C_{2-3}$alkyl-A.

A compound of formula (2) can have the following stereochemistry:

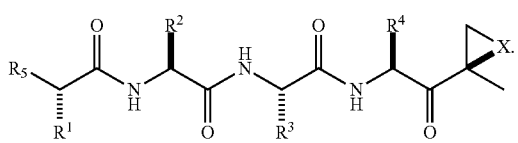

Further non-limiting examples of a compound of formula (2) can be found, for example, in U.S. Pat. No. 7,232,818, which is incorporated by reference, in its entirety herein. In some embodiments, a compound of formula (2) has a low solubility in water.

In some embodiments, a peptide proteasome inhibitor can be a compound of formula (3):

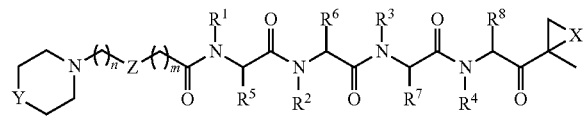

wherein:
X is oxygen, NH, or N($C_{1-6}$ alkyl);
Y is NH, N($C_{1-6}$ alkyl), O, or $C(R^9)_2$;
Z is O or $C(R^9)_2$;
$R_1$, $R^2$, $R^3$, and $R^4$ are all hydrogen;
each $R^5$, $R^6$, $R^7$, $R^8$, and $R^9$ is independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with one or more of an alkyl, amide, amine, carboxylic acid or a pharmaceutically acceptable salt thereof, carboxyl ester, thiol, and thioether;
m is an integer from 0 to 2; and
n is an integer from 0 to 2;
or a pharmaceutically acceptable salt thereof.

In some embodiments, X is O. In some embodiments, Y is N($C_{1-6}$ alkyl), O, or $C(R^9)_2$. In some embodiments, Z is $C(R^9)_2$. In some embodiments, $R^5$, $R^6$, $R^7$, and $R^8$ are independently selected from $C_{1-6}$alkyl, $C_{1-6}$hydroxyalkyl, and $C_{1-6}$aralkyl and each $R^9$ is hydrogen. For example, $R^6$ and $R^8$ are independently $C_{1-6}$alkyl, $R^5$ and $R^7$ are independently $C_{1-6}$aralkyl and each $R^9$ is H. In some embodiments, n is 0 or 1.

In some embodiments, X is O and $R^5$, $R^6$, $R^7$, and $R^8$ are independently selected from $C_{1-6}$alkyl, $C_{1-6}$hydroxyalkyl, and $C_{1-6}$aralkyl. For example, $R^6$ and $R^8$ are independently $C_{1-6}$alkyl and $R^5$ and $R^7$ are independently $C_{1-6}$aralkyl.

In some embodiments, X is O, $R^6$ and $R^8$ are both isobutyl, $R^5$ is phenylethyl, and $R^7$ is phenylmethyl.

In some embodiments, $R^5$, $R^6$, $R^7$, and $R^8$ are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from alkyl, amide, amine, carboxylic acid or a pharmaceutically acceptable salt thereof, carboxyl ester, thiol, and thioether. In some embodiments, at least one of $R^5$ and $R^7$ is $C_{1-6}$aralkyl substituted with alkyl such as perhaloalkyl. For example, $R^7$ is $C_{1-6}$aralkyl substituted with trifluoromethyl.

In some embodiments, Y is selected from N-alkyl, O, and $CH_2$. In certain such embodiments, Z is $CH_2$, and m and n are both 0. In some embodiments, Z is $CH_2$, m is 0, and n is 2 or 3. In some embodiments, Z is O, m is 1, and n is 2.

In some embodiments, a compound of formula (3) is a compound of formula (4):

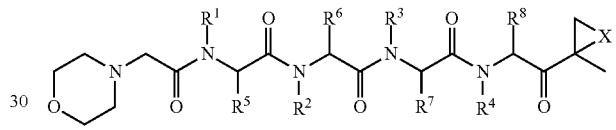

wherein:
X is O, NH, or N-alkyl, preferably O;
$R^1$, $R^2$, $R^3$, and $R^4$ are all hydrogen; and
$R^5$, $R^6$, $R^7$, and $R^8$ are independently selected from hydrogen, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether,
or a pharmaceutically acceptable salt thereof.

In some embodiments, $R^5$, $R^6$, $R^7$, and $R^8$ are independently selected from $C_{1-6}$alkyl, $C_{1-6}$hydroxyalkyl, and $C_{1-6}$aralkyl. For example, $R^6$ and $R^8$ are independently $C_{1-6}$alkyl and $R^5$ and $R^7$ are independently $C_{1-6}$aralkyl.

In some embodiments, X is O and $R^5$, $R^6$, $R^7$, and $R^8$ are independently selected from $C_{1-6}$alkyl, $C_{1-6}$hydroxyalkyl, and $C_{1-6}$aralkyl. For example, $R^6$ and $R^8$ are independently $C_{1-6}$alkyl and $R^5$ and $R^7$ are independently $C_{1-6}$aralkyl.

In some embodiments, X is O, $R^6$ and $R^8$ are both isobutyl, $R^5$ is phenylethyl, and $R^7$ is phenylmethyl.

In some embodiments, a compound of formula III has the following stereochemistry:

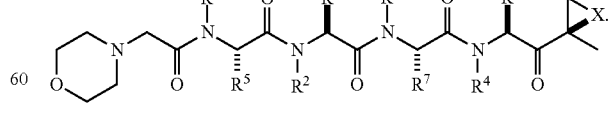

Non-limiting examples of a compound of formula (3) and (4) can be found, for example, in U.S. Pat. No. 7,417,042, which is incorporated by reference in its entirety herein. In some embodiments, a compound of formula (3) or (4) has a low solubility in water.

In some embodiments, a peptide proteasome inhibitor is a compound of formula (5):

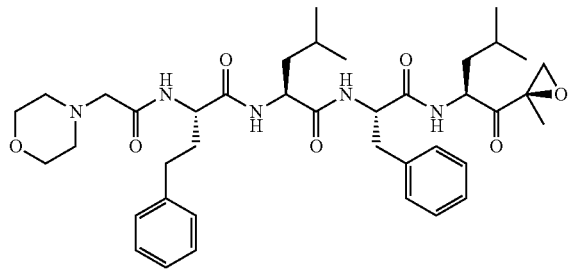 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof. The compound of formula (5) is also known as carfilzomib.

Any of the compounds described herein can be isolated in amorphous or crystalline form. Preparation and purification of crystalline compounds as provided herein can be done as is known in the art, for example, as described in US Publication No. 2009/0105156, which is incorporated by reference in its entirety herein.

In some embodiments, a crystalline compound of formula (5) is substantially pure. In some embodiments, the melting point of the crystalline compound of formula (5) is in the range of about 200 to about 220° C., about 205 to about 215° C., about 211 to about 213° C., or even about 212° C. In some embodiments, a crystalline compound of formula (5) can have a melting point of about 205 to about 215° C. For example, the compound can have a melting point of about 211 to about 213° C. In some embodiments, the DSC of a crystalline compound of formula (5) has a sharp endothermic maximum temperature at about 212° C., e.g., resulting from melting and decomposition of the crystalline form of the compound.

An X-ray powder diffraction pattern of a crystalline compound of formula (5) has characteristic diffraction peaks expressed in degrees 2theta (2θ). For example, a crystalline compound of formula (5) can have a characteristic peak expressed in degrees 2θ at 6.10. In some embodiments, a crystalline compound of formula (5) has a characteristic peak expressed in degrees 2θ at 9.32. In some embodiments, a crystalline compound of formula (5) has a characteristic peak expressed in degrees 2θ at 10.10. In some embodiments, a crystalline compound of formula (5) has a characteristic peak expressed in degrees 2θ at 12.14. In some embodiments, a crystalline compound of formula (5) has a characteristic peak expressed in degrees 2θ at 13.94. In some embodiments, a crystalline compound of formula (5) has a characteristic peak expressed in degrees 2θ at 18.44. In some embodiments, a crystalline compound of formula (5) has a characteristic peak expressed in degrees 2θ at 20.38. In some embodiments, a crystalline compound of formula (5) has a characteristic peak expressed in degrees 2θ at 23.30. In some embodiments, a crystalline compound of formula (5) has an X-ray powder diffraction pattern comprising 2 to 8 characteristic peaks expressed in degrees 2θ at 6.10, 9.32, 10.10, 12.14, 13.94, 18.44, 20.38, and 23.30. For example, a crystalline compound of formula (5) can have an X-ray powder diffraction pattern comprising characteristic peaks expressed in degrees 2θ at 6.10, 9.32, 10.10, 12.14, 13.94, 18.44, 20.38, and 23.30.

In some embodiments, a crystalline compound of formula (5) has a characteristic peak expressed in degrees 2θ at about 6.1. In some embodiments, a crystalline compound of formula (5) has a characteristic peak expressed in degrees 2θ at about 9.3. In some embodiments, a crystalline compound of formula (5) has a characteristic peak expressed in degrees 2θ at about 10.1. In some embodiments, a crystalline compound of formula (5) has a characteristic peak expressed in degrees 2θ at about 12.1. In some embodiments, a crystalline compound of formula (5) has a characteristic peak expressed in degrees 2θ at about 13.9. In some embodiments, a crystalline compound of formula (5) has a characteristic peak expressed in degrees 2θ at about 18.4. In some embodiments, a crystalline compound of formula (5) has a characteristic peak expressed in degrees 2θ at about 20.4. In some embodiments, a crystalline compound of formula (5) has a characteristic peak expressed in degrees 2θ at about 23.3. In some embodiments, a crystalline compound of formula (5) has an X-ray powder diffraction pattern comprising 2 to 8 characteristic peaks expressed in degrees 2θ at about 6.1, 9.3, 10.1, 12.1, 13.9, 18.4, 20.4, and 23.3. In some embodiments, a crystalline compound of formula (5) has an X-ray powder diffraction pattern comprising characteristic peaks expressed in degrees 2θ at about 6.1, 9.3, 10.1, 12.1, 13.9, 18.4, 20.4, and 23.3.

In some embodiments, a crystalline compound of formula (5) has an X-ray powder diffraction pattern having characteristic peaks expressed in degrees 2θ at 6.10; 8.10; 9.32; 10.10; 11.00; 12.14; 12.50; 13.64; 13.94; 17.14; 17.52; 18.44; 20.38; 21.00; 22.26; 23.30; 24.66; 25.98; 26.02; 27.84; 28.00; 28.16; 29.98; 30.46; 32.98; 33.22; 34.52; and 39.46.

In some embodiments, a crystalline compound of formula (5) has an X-ray powder diffraction pattern having characteristic peaks expressed in degrees 2θ at 6.1; 8.1; 9.3; 10.1; 11.0; 12.1; 12.5; 13.6; 13.9; 17.1; 17.5; 18.4; 20.4; 21.0; 22.3; 23.3; 24.7; 25.9; 26.0; 27.8; 28.0; 28.2; 30.0; 30.5; 33.0; 33.2; 34.5; and 39.5.

X-ray powder diffraction (XRPD) analysis was performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by NAI scintillation detector. A θ-2θ continuous scan at 3°/min (0.4 sec/0.02°) from 2.5 to 40° 2θ was used. A silicon standard was analyzed to check the instrument alignment. Data were collected and analyzed using XRD-6100/7000 v.5.0. Samples were prepared for analysis by placing them in an aluminum holder with silicon insert.

In some embodiments, a crystalline compound of formula (5) is a crystalline salt of a compound of formula (5). For example, a crystalline salt of compound of formula (5) can be selected from the group consisting of: a citrate, tartrate, trifluoroacetate, methanesulfonate, toluenesulfonate, hydrochloride, and hydrobromide salts. In some embodiments, a crystalline salt of a compound of formula (5) is a citrate salt. In some embodiments, the crystalline solid may exist as a cocrystal.

In some embodiments, a crystalline citrate salt of a compound of Formula (5) is substantially pure. In some embodiments, the melting point of the crystalline citrate salt of a compound of Formula (5) is in the range of about 180 to about 190° C., for example, about 184 to about 188° C. In some embodiments, the DSC of a crystalline citrate salt of a compound of Formula (5) has a sharp endothermic maximum at about 187° C., e.g., resulting from melting and decomposition of the crystalline form.

In some embodiments, a crystalline compound of formula (5) has an X-ray powder diffraction pattern comprising two or more characteristic peaks expressed in degrees 2θ at 4.40; 7.22; 9.12; 12.36; 13.35; 14.34; 15.54; 16.14; 16.54; 17.00; 18.24; 18.58; 19.70; 19.90; 20.30; 20.42; 21.84; 22.02; 23.34; 23.84; 24.04; 24.08; 24.48; 24.76; 25.48; 26.18; 28.14; 28.20; 28.64; 29.64; 31.04; 31.84; 33.00; 33.20; 34.06; 34.30; 34.50; 35.18; 37.48; 37.90; and 39.48. For example, a crystalline citrate salt of a compound of Formula (5) can have an X-ray powder diffraction pattern having characteristic peaks expressed in degrees 2θ at 4.40; 7.22; 9.12; 12.36; 13.35; 14.34; 15.54; 16.14; 16.54; 17.00; 18.24; 18.58; 19.70; 19.90; 20.30; 20.42; 21.84; 22.02; 23.34; 23.84; 24.04; 24.08; 24.48; 24.76; 25.48; 26.18; 28.14; 28.20; 28.64; 29.64; 31.04; 31.84; 33.00; 33.20; 34.06; 34.30; 34.50; 35.18; 37.48; 37.90; and 39.48.

Pharmaceutical Compositions

The methods provided herein include the manufacture and use of pharmaceutical compositions, which include any of the compounds provided herein. Also included are the pharmaceutical compositions themselves.

In some embodiments, the compounds provided herein can be formulated as described in U.S. Pat. No. 7,737,112.

Also provided herein are cyclodextrin complexation methods for preparing a pharmaceutical composition of a peptide proteasome inhibitor (e.g., a compound of formula (1)-(5) or a pharmaceutically acceptable salt, solvate, hydrate, cocrystal, or polymorph thereof). The method comprises providing a first combination having a peptide proteasome inhibitor, one ore more cyclodextrins, and water, wherein the first combination is heterogeneous and the peptide proteasome inhibitor or salt has a low solubility in the first combination. The method further comprises altering the pH of the first combination to form a second combination, wherein the solubility of the peptide proteasome inhibitor in the second combination is greater than the solubility of the peptide proteasome inhibitor in the first combination. For example, the method can include contacting the first combination with an acid to form the second combination. The second combination may still be heterogeneous, yet can still facilitate a sufficient increase in solubility such that the complexation process can be initiated and progress. This can enable a majority of the inhibitor to be complexed, while as a heterogeneous mixture through partial complexation, or to complete complexation forming a homogeneous solution. In the case of a heterogeneous complexed mixture, once a desired extent of solubilization and complexation has been achieved, the excess solids can be filtered off to yield a homogeneous solution.

The term "complexation" as used herein refers to the formation of an to intermolecular inclusion complex, or an intermolecular association, in solution and between one or more peptide proteasome inhibitors and one or more cyclodextrin molecules. The inclusion and or the association provides utility as a mechanism of substantially increasing the concentration of the inhibitor(s) that can be achieved in aqueous solution compared to aqueous phase dissolution in a similar pH range without the complexing agent (i.e., one or more cyclodextrin molecules). In some embodiments, the cyclodextrin (e.g., SBECD, e.g., from a low chloride:cyclodextrin source, e.g., a low chloride SBECD):inhibitor (e.g., carfilzomib) ratio is 1:1. In other embodiments, more than one cyclodextran (e.g., each independently selected from SBECD, a low chloride:cyclodextrin and a low chloride SBECD) can be complexed to a particular inhibitor (e.g., 2, 3, 4, 5, or 6; e.g., 2 or 3) cyclodextrans (e.g., each independently selected from SBECD, a low chloride:cyclodextrin and a low chloride SBECD) can be complexed to a particular inhibitor (e.g., carfilzomib). In some embodiments, the cyclodextrin (e.g., SBECD, e.g., from a low chloride:cyclodextrin source, e.g., a low chloride SBECD):inhibitor (e.g., carfilzomib) ratio is 1-5:1 (e.g., 1-4:1; 1-3:1; 1-2:1; 2-5:1, 2-4:1, 2-3:1). Complexation ratios can be determined using, e.g., the methods described herein.

A complexed or associated state is apparent when a dissolved concentration of the inhibitor(s) is measurable, via an appropriate conventional analytical method such as HPLC, and the concentration substantially exceeds that achievable via dissolution of inhibitor(s) in water without cyclodextrin(s) present. The complexed or associated solution of inhibitor(s) and cyclodextrin(s) can be prepared so as to exceed the concentration in aqueous solution where the cyclodextrin(s) are absent which is useful for formulating a medicinal compound of convenient injection volume and delivered dose. Further, the complexed or associated solution of inhibitor(s) exhibit physical stability (or otherwise described as metastability) where the inhibitor remains in a homogeneous solution (without precipitation or crystallization of solid particles) for longer time periods than typical for solutions of the inhibitor without a cyclodextrin present. Due to this extended duration of remaining a clear solution, crystal nucleation and subsequent depletion of supersaturation does not occur for all practical conditions of use as a medicinal formulation. An indexing approach described herein can be used to model and determine cyclodextran:inhibitor ratios.

Many small molecule organic compound drugs have pH dependent solubility. It is frequent that a pH range appropriate for administration of a drug (such as by injection where the tolerable pH range is generally considered from 3-10.5 for intravenous administration) is not in the same pH where sufficient solubility of the drug can be found in aqueous solution (for example at or below pH 2). To enable a pharmaceutically useful concentration level of drug in solution at a pH range acceptable and tolerable for administration (e.g. by injection), complexation or association of the drug with cyclodextrin(s) as claimed here is a practical method. It can increase the concentration in solution that can be achieved within the pH range tolerable for administration. Such an increase in concentration could be for example from initially 1-100 micrograms per milliliter without cyclodextrin(s), increased up to 500-10,000 micrograms per milliliter with cyclodextrin(s). Complexation or association is thereby a technology that enables an otherwise poorly water soluble compound to be sufficiently solubilized and developed as a pharmaceutically useful compound. Those skilled in the art understand that the amount of cyclodextrin(s) required to achieve a desired concentration and physical stability state can vary. Accordingly, the amount of cyclodextrin may be determined on an individual combination basis using well-known methods.

For basic drug molecules, solubility is usually enhanced at lower pH. This also presents stability and shelf life challenges in some instances if used without complexing or associating agents such as cyclodextrin(s). For example, sufficient solubility may be achieved via lowering the pH of a solution with an acid, however such pH reduction may lead to degradation reactions from the acidic conditions. See Table 1 for intrinsic aqueous solubility data for carfilzomib, showing some moderate increase in solubility with lowering of pH.

TABLE 1

| Solvent | Aqueous solubility of carfilzomib as a function of pH, without cyclodextrins Solubility (mg/mL) |
|---|---|
| Water | 0.002 |
| Water/pH 5 | 0.002 |
| Water/pH 3 | 0.02 |
| Water/pH 1 | 1.8 |

Numerous acid mediated degradation reaction pathways exist for small molecule drugs and biological molecules, such as hydrolysis of amides in smaller inactive peptide fragments, or hydrolytic opening of functional epoxides moieties. The products of acid mediated degradation may lack pharmacological activity, and may be toxic or genotoxic compounds even at trace levels. Complexing or associating compounds at pH conditions where significant degradation is avoided further expands the utility of cyclodextrins to facilitate the clinical and commercial development of compounds that are have pH dependent stability characteristics.

In order to balance the competing needs of avoiding acid mediated degradation side reactions which occur at low pH with increasing the rate of complexation via lowering the pH, a unique pH condition was found. Surprisingly, the pH of an aqueous solution achieved via the addition of certain concentrations of acids, for example citric acid (around pH 2.5 to 3.0), was found to be sufficient to decrease the pH to initiate complexation without initiating significant levels of degradation side reactions. In this state, the inhibitor was partially solubilized by the pH condition, but not entirely. As a result, a heterogeneous mixture existed (e.g., a slurry) of the inhibitor partly dissolved in the aqueous solution of cyclodextrin and citric acid, and partly existing as solid particles (crystals) of the inhibitor. Over time (typically several hours to a day), the dissolved fraction of inhibitor would become complexed or associated with the cyclodextrin. This process would enable more of the solid particles of inhibitor to dissolve and then become complexed. Over time, mass transfer can occur from initially solid phase inhibitor, to dissolved phase inhibitor, to a dissolved complexed state of the cyclodextrin-inhibitor. More commonly, cyclodextrin complexation is achieved via formation of a homogeneous solution of the compound to be complexed. For carfilzomib, the formation of a homogenous solution would require a very low pH where degradation reactions, such as those with the strong acid hydrogen chloride forming potential genotoxic impurities, would occur. In this instance, it was practical and useful to perform the complexation process in a heterogeneous state at the milder pH condition of 2.5-3.0 using citric acid, a weak carboxylic acid. Once the target concentration of complexed inhibitor was achieved, the slurry complexation process was terminated by filtering off any undissolved solid particles of the inhibitor. The resulting homogeneous solution could then be adjusted for pH as necessary to a pH range suitable for intravenous administration (e.g., pH 3.5 using aqueous sodium hydroxide). Further, the homogeneous pH adjusted complexed solution could be diluted with water to the exact concentration desired for the next step of the product manufacture and to ensure the label strength of the medicinal product was precise.

The combined effect of cyclodextrin concentration and pH on complexation has a greater solubilization capacity than if either technique was used alone. Solubilization extents are relatively independent of temperature which is convenient for manufacture to maintain cold conditions more preferable for sterile product manufacture and minimizing any temperature accelerated degradation reactions.

A second combination includes complexes of a peptide proteasome inhibitor and cyclodextrin(s). Such complexes have improved water solubility over the peptide proteasome inhibitor alone. For example, homogenous solutions of a compound of formula (5) (carfilzomib) can be obtained at a pharmaceutically useful pH (e.g., about 3.5) and at higher concentrations (e.g., about 5 mg/mL) than could be obtained without one or more cyclodextrins and the processes of complexation between the compound and one or more cyclodextrins provided herein.

In addition to increasing the solubility of a peptide proteasome inhibitor in solution, the formulations prepared by the methods provided herein result in pharmaceutical solutions having surprising stability. Although the high concentrations of proteasome inhibitor achieved by the processing methods provided herein may not be expected to be thermodynamically stable, the solutions have been shown to be unaffected by storage temperature (e.g., the solutions can be stable from −20° C. to 25° C.), freeze thaw cycling, and lyophilization and reconstitution. The stability of complexed peptide proteasome inhibitor and cyclodextrin is sufficient to tolerate adjustments to pH following complexation without precipitation. This solution stability allows for use of the complexed material in a pH range acceptable for injection, stability of the product, and other pharmaceutical purposes. Accordingly, the pharmaceutical compositions prepared by the methods provided herein can, for pharmaceutical uses, be considered supersaturated solutions that do not precipitate or decrease in concentration to a significant extent during their use in any number of medical applications (e.g., a final pharmaceutical composition may be stable for a range of at least 1-5 days, and potentially longer).

A first combination can be prepared by adding a solid form of the peptide proteasome inhibitor to an aqueous solution of one or more cyclodextrins. In some embodiments, when the peptide proteasome inhibitor is a compound of formula (5) or a pharmaceutically acceptable salt thereof, the concentration of the one or more cyclodextrins in the solution is from less than about 1% up to potentially as high as the solubility limit of the cyclodextrins(s), for example, about 40%. In some embodiments, for purposes of manufacture, the concentration of the one or more cyclodextrins in solution is from about 15% to about 30%. In some embodiments, for purposes of reconstitution of the finished drug product as a solution for therapeutic administration or ready for further dilution prior to administration, the concentration of the one or more cyclodextrins in solution is from about 5% to about 15%, for example, approximately 10%. Upon further dilution, this concentration could be reduced further as deemed appropriate for injection or other routes of drug delivery. The mole ratio of the one or more cyclodextrins in the solution to the compound of formula (5) is from about 0.5 to about 100. In some embodiments, this ratio exists as a molar excess of cyclodextrin to shift the complexation stability equilibrium to prefer the complexed state rather than the uncomplexed state. For example, the mole ratio (cyclodextrin moles divided by proteasome inhibitor moles) is from about 10 to about 20. In some embodiments, the weight/weight ratio of cyclodextrin to proteasome inhibitor is about 30 to about 60. Excessive foaming of cyclodextrin solutions can be a complication for robust manufacturing processes. Surprisingly, adding the peptide proteasome inhibitor to the aqueous solution of cyclodextrin(s) can control foaming of the solution in the first combination.

In some embodiments, a first combination consists essentially of a peptide proteasome inhibitor, a cyclodextrin, and water.

The solid form of the peptide proteasome inhibitor added to the solution of cyclodextrin and water can be a crystalline form of the compound as described herein (e.g., the compound can be polymorphic or a specific polymorph as described herein). In some embodiments, the solid form of the peptide proteasome inhibitor is amorphous.

The first combination is heterogenous (e.g., a suspension or slurry). Such a solution can be characterized by the weight percent total solids and particle size distribution of the solution. For example, when the peptide proteasome inhibitor is a compound of formula (5) or a pharmaceutically acceptable salt thereof, the first combination can have a weight percent total solids from about 1% to about 45% (e.g., from about 1% to about 40%; from about 1% to about 35%; from about 1% to about 30%; from about 1% to about 25%; from about 1% to about 20%; from about 1% to about 15%; from about 1% to about 10%; from about 5% to about 45%; from about 10% to about 45%; from about 12% to about 45%; from about 15% to about 45%; from about 20% to about 45%; from about 25% to about 45%; from about 30% to about 45%; from about 35% to about 45%; from about 5% to about 35%; from about 10% to about 40%; from about 15% to about 37%; and from about 18% to about 36%). In some embodiments, the first combination can have a weight percent solids from about 20% to about 33%. In some embodiments, the first combination can have a weight percent solids from about 30% to about 33%. Over the time course of manufacture the proportion of solids which are dissolved versus the proportion undissolved can vary depending on solubility and extent of complexation. Initially, the one or more cyclodextrins are very soluble in water, and the inhibitor is sparingly soluble, thereby remaining mostly as a heterogeneous mixture or slurry.

In some embodiments, the first combination has a particle size distribution with primary particles of diameter ranging from less than about 1 micrometer to about 300 micrometers or more (e.g., from about 1 µm to about 200 µm; from about 1 µm to about 150 µm; from about 1 µm to about 125 µm; from about 1 µm to about 100 µm; from about 1 µm to about 50 µm; from about 1 µm to about 10 µm; from about 5 µm to about 300 µm; from about 25 µm to about 300 µm; from about 50 µm to about 300 µm; from about 60 µm to about 300 µm; from about 75 µm to about 300 µm; from about 100 µm to about 300 µm; from about 125 µm to about 300 µm; from about 150 µm to about 300 µm; from about 200 µm to about 300 µm; from about 225 µm to about 300 µm; from about 250 µm to about 300 µm; from about 5 µm to about 150 µm; from about 25 µm to about 200 µm; from about 50 µm to about 125 µm; from about 10 µm to about 100 µm; from about 75 µm to about 225 µm; and from about 100 µm to about 200 µm). Primary particles may exist as discrete particles or as agglomerates comprised of one or many primary particles. Agglomerates of primary particles may have substantially larger sizes than primary particles. Thereby it is useful to incorporate a high energy mixing device, such as a high shear mixer (often configured as a rotor stator mixer), in addition to a general suspending impeller mixer. The high energy mixer over the time course of about 5 minutes to about 90 minutes (e.g., about 5 minutes to about 80 minutes; about 5 minutes to about 75 minutes; about 5 minutes to about 60 minutes; about 5 minutes to about 45 minutes; about 5 minutes to about 30 minutes; about 10 minutes to about 90 minutes; about 15 minutes to about 90 minutes; about 30 minutes to about 90 minutes; about 45 minutes to about 90 minutes; about 45 minutes to about 90 minutes; about 50 minutes to about 90 minutes; about 75 minutes to about 90 minutes; about 15 minutes to about 75 minutes; about 20 minutes to about 70 minutes; about 30 minutes to about 70 minutes; about 45 minutes to about 75 minutes; and about 10 minutes to about 45 minutes), for example, over the time course of about 60 minutes will break up large agglomerates into dispersed primary particles in the solution of cyclodextrin. Further mixing can assist by breaking up primary particles into smaller fragments of primary particles. This process design facilitates a robust method where the mixing system(s) achieve essentially dispersed primary particles of size distribution ranging from less than about 1 micrometer up to about 30 micrometers, for example, up to about 10 micrometers independent of the size distribution and degrees of agglomeration of the proteosome inhibitor solids. Therefore batch to batch variability of particle size distribution of the proteosome inhibitor is not significant to process performance as the mixing system(s) reduce agglomerates and primary particles typically into the preferable particle size distribution range. For example, the first combination can have a particle size distribution initially from less than about 1 micrometer up to about 10,000 micrometers to a size distribution of less than about 1 micrometer up to about 30 micrometers after application of the high energy mixing step.

In some embodiments, the first combination is substantially free of organic solvent. For example, the water in the first combination can be water for injection (WFI). In some embodiments, the first combination is substantially free of buffer (e.g., the first combination lacks a buffer acid or buffer base).

The method can further comprise mixing the first combination prior to altering the pH of the first combination such as by use of a high shear mixer and a regular impeller. The general mixer can be operated, for example, at any rotational speed sufficient to maintain suspension of particles off the bottom of the mixing tank. Mixing speed is a function of the tank and impeller geometry among other factors and is sufficiently determined by those skilled in the art via visual appearance of the mixing slurry or solution. Likewise, the speed of the high shear mixer is dependent on, for example, the diameter of the mixing element, the stator geometry, the gap width, and other factors. Energy input to the slurry can be determined via theoretic calculations or via empirical measurements. Alternatively, the necessary high shear mixing speed and duration of high speed operation can be determined by those skilled in the art via microscopic observation of slurry samples following various mixing speeds and time combinations. Once disagglomeration and primary particles have been reduced, excess high shear mixing speed and time may be applied without detriment to the process. For example, in some embodiments, the mixing can include stirring the first combination at a rate of from about 500 rpm to about 10,000 rpm. For example, the high shear mixing can be carried out at a speed of about 2,000 rpm to about 3,500 rpm. For smaller and larger mixer and tank diameters, the relevant speeds can change significantly.

Mixing of the first combination can be carried out at a temperature of from about 0° C. to about 30° C. (e.g., from about 5° C. to about 25° C.; from about 10° C. to about 30° C.; from about 15° C. to about 25° C.; from about 5° C. to about 20° C.; from about 2° C. to about 22° C.; and from about 20° C. to about 30° C.). In some embodiments, mixing of the first combination is carried out for a time sufficient to achieve a particle size distribution ranging from less than about 1 micrometer to about 30 micrometers in the first combination. Mixing of the first combination is carried out for a time period of from about 30 minutes to about 90 minutes, for example 60 minutes.

Altering the pH of the first solution can include increasing or decreasing the pH of the first solution by addition of an acid or a base. In some embodiments, when the peptide proteasome inhibitor is a compound of formula (5) or a pharmaceutically acceptable salt thereof, the pH of the first combination is about 4 to about 7. In some embodiments, an acid, is added to alter the pH, such as an inorganic or an organic acid. Non-limiting examples of acids include lactic acid, acetic acid, formic acid, citric acid, oxalic acid, uric acid, succinic acid, maleic acid, fumaric acid, benzoic acid, tartaric acid, glycine hydrochloride, bisulfate (existing, for example, as a sodium, potassium, or ammonium salt), and phosphoric acid or salts of phosphate. In some embodiments, the acid is an organic acid. In some embodiments, the acid is citric acid. A suitable acid can have one or more pKa values, with a first pKa of from about −6 to about +5. For example, the acid has a first pKa in the range of about +1 to about +4.5. In some embodiments, the acid has a first pKa in the range of about +1.5 to about +3.5. See, for example, *Handbook of Pharmaceutical Salts: Properties, Selection, and Use*, Eds. P. Heinrich Stahl and Camille G. Wermuth, Verlag Helvetica Chimica Acta (Switzerland) 2002, 336-341, which is incorporated by reference in its entirety herein.

In some embodiments, for compounds where the solubility and complexation is in fact enhanced via increasing pH, the pH is altered by addition of a base, for example, an inorganic or an organic base. Non-limiting examples of inorganic bases include sodium hydroxide, potassium hydroxide, ammonium hydroxide, calcium hydroxide, magnesium hydroxide, and carbonate or bicarbonate salts of sodium, potassium, or ammonium. Non-limiting examples of organic bases include pyridine, methyl amine, triethyl amine, imidazole, benzimidazole, histidine, and a phosphazene base. An organic base can have a pKb or a first pKb of from about −6 to about +10. The relevant pKa or pKb of the acid or base respectively needs to be in a range sufficient to achieve some increase in the solubility of the inhibitor. In some embodiments, the acid or base is added in the form of an aqueous solution (e.g., an aqueous solution of an acid).

Altering the pH of the first solution results in the formation of a second combination where the peptide proteasome inhibitor is more soluble than in the first combination. For example, a peptide proteasome inhibitor can be at least about 10% more soluble (e.g., at least about 100%, at least about 150%, at least about 200%, at least about 250%, at least about 400%, at least about 500%, at least about 1000%, at least about 1250%, at least about 1500%, at least about 2000%, at least about 2500%, at least about 3000%, at least about 4000%, at least about 5000%, at least about 5500%, at least about 6000%, at least about 7500%, at least about 8000%, at least about 9000%, and at least about 10,000% more soluble) in the second combination compared to the solubility of the inhibitor in the first combination.

Without being bound by theory, altering the pH of the first combination initiates complexation of the one or more cyclodextrins and the peptide proteasome inhibitor. Increasing complexation alters the equilibrium of the solution, triggering additional complexation, and ultimately results in the solubilization of the peptide proteasome inhibitor. Following addition of the additive, the second combination can be mixed for a time sufficient to achieve either a heterogeneous mixture with sufficiently solubilized and complexed inhibitor, or a homogenous third combination where all the inhibitor has been complexed and none remains as undissolved solids. For example, the concentration of the proteasome inhibitor in the third combination can be from about 1 to about 18 mg/mL, for example, about 2 to about 8 mg/mL, about 4 to about 6 mg/mL, or about 5 to about 6 mg/mL. In some embodiments, the pH of the third combination is from about 1.5 to about 4, for example, about 2 to about 3.5 or about 2.5 to about 3.5. Considering the instances where sufficient complexation can be achieved without necessarily dissolving and complexing the entire mass of inhibitor present as a slurry, it may be useful to terminate the complexing process once a target concentration has been achieved. In these instances, a homogeneous solution of desired concentration of the inhibitor can be achieved via filtration of the excess solid content of the inhibitor. This leaves the complexed inhibitor and cyclodextrin(s) in a functionally stable solution, even though the dynamic equilibrium of complexation and solubilization may imply a non-thermodynamically stable state.

Complexation of the peptide proteasome inhibitor in the third combination is at least about 50% (e.g., at least about 55%, at least about 60%, at least about 65%, at least about 70%, at least about 75%, at least about 80%, at least about 85%, at least about 90%, at least about 92%, at least about 94%, at least about 95%, at least about 96%, at least about 97%, at least about 98%, at least about 99%). In some embodiments, the complexation of the peptide proteasome inhibitor in the third combination is at least about 99%. Conceivably, for some combinations of cyclodextrin concentration, inhibitor concentration, pH, and complexation time, a 100% complex solution of the inhibitor can be prepared, where the mixture becomes homogeneous.

In some embodiments, the method described above is performed in a single vessel. For example, mixing the complexing slurry in the method can be performed using a probe style high shear mixer (e.g., a homogenizer) inside a temperature controlled jacketed mixing tank.

Provided herein is a method for preparing a pharmaceutical composition of a compound of formula (5) or a pharmaceutically acceptable salt form thereof, the method comprising providing a first combination of a compound of formula (5), one or more cyclodextrins, and water, wherein the first combination is heterogenous and the compound or salt has a low solubility in the first combination. In some embodiments, at least one of the one or more cyclodextrins is SBECD and the water is WFI. The method further comprises contacting the first combination with an acid to form a second combination, wherein the compound is more soluble in the second combination than in the first combination. In some embodiments, the acid is an citric acid (e.g., an aqueous solution of citric acid).

A non-limiting example of the method includes providing a first combination including water (e.g., WFI), SBECD, and the compound of formula (5) or a pharmaceutically acceptable salt thereof in a vessel. In some embodiments, the water and SBECD are mixed prior to addition of the compound. The first combination can be mixed until a heterogenous solution is achieved (e.g., from about 30 to about 90 minutes, from about 40 to about 80 minutes, and from about 50 to about 70 minutes). In some embodiments, the first combination is mixed for about 60 minutes. Should the compound agglomerate in the first combination, the particle size for any agglomerated compound can be reduced. Once a heterogenous mixture (e.g., a slurry) is achieved, an acid is added (e.g., an organic acid such as citric acid) to the first combination to prepare a second combination. In some embodiments the acid is added as an aqueous solution. Mixing can then be continued until a homogenous third combination is prepared, or for lesser time periods remaining as a heterogeneous mixture with a desired extent of complexation and solubilization achieved. In some embodiments, mixing of the second combination is conducted for a time ranging from about 1 to about 48 hours, for example, up to 18 hours. In some embodiments, mixing of the second combination is conducted for about 12 hours. For example, mixing can be conducted for about six hours. In some embodiments, a concentration of the compound in the third combination ranges from about 1 to about 15 mg/mL (e.g., from about 3 to about 12 mg/mL, from about 4 to about 8 mg/mL, about 5 mg/mL). In some embodiments, the method is used to prepare a solution of the compound for injection. In other embodiments, the method is used to prepare a solution for lyophilization as an aseptic finished pharmaceutical product which can be stored, transported, and reconstituted with water or other vehicle when ready for injection to a patient.

The pharmaceutical compositions obtained as sterile products using the procedures described herein are typically manufactured applying aseptic techniques and sterile filtration before filling into the primary packaging unit (e.g. glass vials), unless the preparation involved a sterilization step and no contamination occurs prior to use.

The peptide proteasome inhibitor composition dissolved in aqueous buffer or in aqueous solution, for example, following sterile filtration, can optionally be lyophilized (in a contaminant-free and -proof container) and reconstituted in appropriate aqueous diluent just prior to use. In certain embodiments, a lyophilized pharmaceutical composition as provided herein includes e.g., carfilzomib, e,g, KYPROLIS, which contains 60 mg of carfilzomib, 3000 mg sulfobutylether beta-cyclodextrin, 57.7 mg citric acid, and sodium hydroxide for pH adjustment (target pH 3.5)).

In some embodiments, the diluent is sterile water for injection (WFI). In some embodiments, the diluent is a sterile buffer (e.g., a citrate buffer). In some embodiments, the diluent comprises citric acid. In certain embodiments, reconstitution can be carried out according to the following protocol (e.g., to achieve a carfilzomib concentration of 2 mg/mL):
1. Remove vial from refrigerator just prior to use.
2. Aseptically reconstitute each vial by slowly injecting 29 mL Sterile Water for Injection, USP, directing the solution onto the INSIDE WALL OF THE VIAL to minimize foaming.
3. Gently swirl and/or invert the vial slowly for about 1 minute, or until complete dissolution of any cake or powder occurs. DO NOT SHAKE to avoid foam generation. If foaming occurs, allow solution to rest in vial for about 2 to 5 minutes, until foaming subsides.
4. After reconstitution, KYPROLIS is ready for intravenous administration. The reconstituted product should be a clear, colorless solution. If any discoloration or particulate matter is observed, do not use the reconstituted product.
5. When administering in an intravenous bag, withdraw the calculated dose from the vial and dilute into 50 mL 5% Dextrose Injection, USP intravenous bag.
6. Immediately discard the vial containing the unused portion.

In the compositions provided herein, one source of pH control is a buffer. Typically, a buffer is present as an acid or a base and its conjugate base or acid, respectively. In one embodiment, the range of buffering salt is 1-100 mM. For example, the range of buffering salt can be 5-50 mM (e.g., about 10 mM (in solid formulations, the amount of buffer is selected to produce this concentration after reconstitution/dilution)). The concentration of buffer and the pH of the solution can be chosen to give optimal balance of solubility and stability.

Examples of suitable buffers include mixtures of weak acids and alkali metal salts (e.g., sodium, potassium) of the conjugate base of weak acids such as sodium tartrate and sodium citrate. In some embodiments, the buffer is sodium citrate/citric acid.

The solubilization of poorly water-soluble drugs by cyclodextrin complexation has been extensively studied. Cyclodextrins are cyclic oligosaccharides consisting of 6, 7, or 8 glucose units (α-CD, β-CD, and γ-CD) joined by α-1,4 bonds. The internal diameters of α-CD, β-CD, and γ-CD are approximately 5 Å, 6 Å, and 8 Å, respectively. The interior cavity is relatively hydrophobic due to the $CH_2$ and ether groups, whereas the exterior, consisting of primary and secondary hydroxyl groups, is more polar. Water inside the cavity tends to get replaced by more non-polar molecules. The ability of cyclodextrins to form non-covalent inclusion complexes with molecules that partially fit inside its non-polar cavity leads to drug solubilization.

Two water-soluble β-CD derivatives of pharmaceutical interest are sulfobutyl ether beta-cyclodextrin (SBECD) and hydroxypropyl beta-cyclodextrin (HPCD), both of which have been shown to be safe and well tolerated. Both SBECD (brand name Captisol®) and HPCD (brand name Kleptose®) are used in commercially available intravenous products.

Cyclodextrins, as provided herein, include alpha-, beta- and gamma-cyclodextrin. In one embodiment, the one or more cyclodextrins are either a substituted or non-substituted β-cyclodextrin, present, for example, at from 5-35% (w/v). In some embodiments, the amount of a cyclodextrin is about 25% (w/v). In a certain embodiment, the amount of a cyclodextrin in a formulation suitable for injection is about 10% (w/v). In another embodiment, the one or more cyclodextrins are a substituted β-cyclodextrin. Substituted cyclodextrins increase the solubility of the cyclodextrin and mitigate toxic effects associated with unsubstituted cyclodextrins. Examples of substituted β-cyclodextrins include those substituted with one or more hydrophilic groups, such as monosaccharide (e.g., glucosyl, maltosyl), carboxyalkyl (e.g., carboxylmethyl, carboxyethyl), hydroxyalkyl-substituted (e.g., hydroxyethyl, 2-hydroxypropyl) and sulfoalkylether-substituted beta-cyclodextrin. Particularly suitable beta-cyclodextrins include hydroxypropyl beta-cyclodextrin (HPBCD) and sulfobutylether beta-cyclodextrin (SBECD). In some embodiments, the cyclodextrin is SBECD. However, it is understood that typically any substitution to the cyclodextrin, including substitution by hydrophobic groups such as alkyls, will improve its aqueous solubility by disrupting the hydrogen-bonding network within the crystal lattice of the solid cyclodextrin, thereby lowering the lattice energy of the solid. The degree of substitution is not believed to be critical; however, in some embodiments, the degree of substitution is at least 1% and typically 2% to 10%, such as 3% to 6%.

In some embodiments, one or more cyclodextrins may be used. For example, a mixture of two or more cyclodextrins can be used to complex a peptide proteasome inhibitor provided herein. In some embodiments, captisol and kleptose may be used to complex a peptide proteasome inhibitor such as carfilzomib.

The inventors have discovered that it can be advantageous to minimize the amount of chloride ion (or other nucleophilic anions) in the methods and pharmaceutical compositions described herein.

In some embodiments, at least one of the one or more cyclodextrins (added to the first combination) is a low chloride cyclodextrin. As used herein, a "low chloride cyclodextrin" refers to a chloride-containing cyclodextrin having less than or equal to 0.05% w/w sodium chloride, or if a chloride source(s) other than (or in addition to) sodium chloride is/are present, a "low chloride cyclodextrin" refers to a chloride-containing cyclodextrin having a chloride ion content that is less than or equal to the amount of chloride that would be present in a cyclodextrin having 0.05% w/w sodium chloride. In some embodiments, the low chloride cyclodextrin is a low chloride SBECD. The determination of chloride concentration can be determined by a variety of methods known in the art (e.g., for commercially obtained cyclodextrans from the manufacturer's product specification, e.g., by gravimetric techniques, e.g., by potentiometric techniques).

In some embodiments, at least one of the one or more cyclodextrins (added to the first combination) does not include a detectable amount of chloride ion.

In some embodiments, the amount of chloride ion present is sufficiently low so as to provide a shelf life of 2 years when stored at 2-8 degrees C. In certain embodiments, chloride ion is present, and the amount of chloride ion present is sufficiently low so as to provide a shelf life of 2 years when stored at 2-8 degrees C.

In some embodiments, the mole ratio of chloride ion to compound in the first combination is not more than 2.0. In certain embodiments, at least some chloride ion is present (i.e., the mole ratio of chloride ion to compound in the first combination is other than 0, but less than 2.0).

In some embodiments, the mole ratio of chloride ion to compound in the first combination is not more than 1.5. In certain embodiments, at least some chloride ion is present (i.e., the mole ratio of chloride ion to compound in the first combination is other than 0, but less than 1.5).

In some embodiments, the mole ratio of chloride ion to compound in the first combination is not more than 1.2. In certain embodiments, at least some chloride ion is present (i.e., the mole ratio of chloride ion to compound in the first combination is other than 0, but less than 1.2).

In some embodiments, the mole ratio of chloride ion to compound in the first combination is not more than 1.0. In certain embodiments, at least some chloride ion is present (i.e., the mole ratio of chloride ion to compound in the first combination is other than 0, but less than 1.0).

In some embodiments, the mole ratio of chloride ion to compound in the first combination is not more than 0.9. In certain embodiments, at least some chloride ion is present (i.e., the mole ratio of chloride ion to compound in the first combination is other than 0, but less than 0.9).

In some embodiments, the mole ratio of chloride ion to compound in the first combination is not more than 0.8. In certain embodiments, at least some chloride ion is present (i.e., the mole ratio of chloride ion to compound in the first combination is other than 0, but less than 0.8).

In some embodiments, the mole ratio of chloride ion to compound in the first combination is not more than 0.7. In certain embodiments, at least some chloride ion is present (i.e., the mole ratio of chloride ion to compound in the first combination is other than 0, but less than 0.7).

In some embodiments, the mole ratio of chloride ion to compound in the first combination is not more than 0.6. In certain embodiments, at least some chloride ion is present (i.e., the mole ratio of chloride ion to compound in the first combination is other than 0, but less than 0.6).

In some embodiments, the mole ratio of chloride ion to compound in the first combination is not more than 0.5. In certain embodiments, at least some chloride ion is present (i.e., the mole ratio of chloride ion to compound in the first combination is other than 0, but less than 0.5).

In some embodiments, the mole ratio of chloride ion to compound in the first combination is not more than 0.4. In certain embodiments, at least some chloride ion is present (i.e., the mole ratio of chloride ion to compound in the first combination is other than 0, but less than 0.4).

In some embodiments, the mole ratio of chloride ion to compound in the first combination is not more than 0.3. In certain embodiments, at least some chloride ion is present (i.e., the mole ratio of chloride ion to compound in the first combination is other than 0, but less than 0.3).

In some embodiments, the mole ratio of chloride ion to compound in the first combination is not more than 0.2. In certain embodiments, at least some chloride ion is present (i.e., the mole ratio of chloride ion to compound in the first combination is other than 0, but less than 0.2).

In some embodiments, the mole ratio of chloride ion to compound in the first combination is not more than 0.1. In certain embodiments, at least some chloride ion is present (i.e., the mole ratio of chloride ion to compound in the first combination is other than 0, but less than 0.1).

In some embodiments, the mole ratio of chloride ion to compound in the first combination is from 0.2 to 1.2 (e.g., 0.3 to 1.2, e.g., 0.2 to 0.4, e.g., 0.3 to 0.4, e.g., 0.32).

In embodiments, the mole ratios of chloride ion to compound described herein can also be present in the second and/or third combinations.

In one aspect, pharmaceutical compositions are featured, which are prepared by any one of the methods described herein and have a mole ratio of chloride ion to compound that is not more than 2.0. In certain embodiments, at least some chloride ion is present (i.e., the mole ratio of chloride ion to compound in the pharmaceutical compositions is other than 0, but less than 2.0).

In some embodiments, the mole ratio of chloride ion to compound in the pharmaceutical compositions is not more than 1.5. In certain embodiments, at least some chloride ion is present (i.e., the mole ratio of chloride ion to compound in the pharmaceutical compositions is other than 0, but less than 1.5).

In some embodiments, the mole ratio of chloride ion to compound in the pharmaceutical compositions is not more than 1.2. In certain embodiments, at least some chloride ion is present (i.e., the mole ratio of chloride ion to compound in the pharmaceutical compositions is other than 0, but less than 1.2).

In some embodiments, the mole ratio of chloride ion to compound in the pharmaceutical compositions is not more than 1.0. In certain embodiments, at least some chloride ion is present (i.e., the mole ratio of chloride ion to compound in the pharmaceutical compositions is other than 0, but less than 1.0).

In some embodiments, the mole ratio of chloride ion to compound in the pharmaceutical compositions is not more than 0.9. In certain embodiments, at least some chloride ion is present (i.e., the mole ratio of chloride ion to compound in the pharmaceutical compositions is other than 0, but less than 0.9).

In some embodiments, the mole ratio of chloride ion to compound in the pharmaceutical compositions is not more than 0.8. In certain embodiments, at least some chloride ion is present (i.e., the mole ratio of chloride ion to compound in the pharmaceutical compositions is other than 0, but less than 0.8).

In some embodiments, the mole ratio of chloride ion to compound in the pharmaceutical compositions is not more than 0.7. In certain embodiments, at least some chloride ion is present (i.e., the mole ratio of chloride ion to compound in the pharmaceutical compositions is other than 0, but less than 0.7).

In some embodiments, the mole ratio of chloride ion to compound in the pharmaceutical compositions is not more than 0.6. In certain embodiments, at least some chloride ion is present (i.e., the mole ratio of chloride ion to compound in the pharmaceutical compositions is other than 0, but less than 0.6).

In some embodiments, the mole ratio of chloride ion to compound in the pharmaceutical compositions is not more than 0.5. In certain embodiments, at least some chloride ion is present (i.e., the mole ratio of chloride ion to compound in the pharmaceutical compositions is other than 0, but less than 0.5).

In some embodiments, the mole ratio of chloride ion to compound in the pharmaceutical compositions is not more than 0.4. In certain embodiments, at least some chloride ion is present (i.e., the mole ratio of chloride ion to compound in the pharmaceutical compositions is other than 0, but less than 0.4).

In some embodiments, the mole ratio of chloride ion to compound in the pharmaceutical compositions is not more than 0.3. In certain embodiments, at least some chloride ion is present (i.e., the mole ratio of chloride ion to compound in the pharmaceutical compositions is other than 0, but less than 0.3).

In some embodiments, the mole ratio of chloride ion to compound in the pharmaceutical compositions is not more than 0.2. In certain embodiments, at least some chloride ion is present (i.e., the mole ratio of chloride ion to compound in the pharmaceutical compositions is other than 0, but less than 0.2).

In some embodiments, the mole ratio of chloride ion to compound in the pharmaceutical compositions is not more than 0.1. In certain embodiments, at least some chloride ion is present (i.e., the mole ratio of chloride ion to compound in the pharmaceutical compositions is other than 0, but less than 0.1).

In some embodiments, the pharmaceutical compositions do not include a detectable amount of chloride ion.

In the methods described herein, the compositions provided herein (e.g., solutions of cyclodextrin, first combinations, second combinations, third combinations, and pharmaceutical compositions) have low concentrations of any strong nucleophilic ion (e.g., chloride ion, bromide ion, fluoride ion, and iodide ion). For example, a solution can have a nucleophilic ion concentration of up to and including $8.5 \times 10^{-3}$ M. In some embodiments, solutions having low nucleophilic ion can be purchased commercially or may be prepared using technology known in the art, including, for example, nanofiltration, ultrafiltration, diafiltration, ion exchange chromatography, reverse osmosis, and electrolysis.

In some embodiments, a pharmaceutical composition as provided herein comprises up to and including $8.5 \times 10^{-3}$ M of a nucleophilic ion. In some embodiments, the nucleophilic ion is present as a salt, for example, a sodium salt, but the nucleophilic salt could exist in solution with other cations than sodium (e.g. hydrogen, potassium, magnesium, and calcium cations). In some embodiments, a pharmaceutical composition as provided herein comprises up to $8.5 \times 10^{-3}$ M of a nucleophilic ion. For example, a pharmaceutical composition comprises less than $8.5 \times 10^{-3}$ M of a nucleophilic ion.

In the methods described herein, the compositions provided herein (e.g., solutions of cyclodextrin, first combinations, second combinations, third combinations, and pharmaceutical compositions) have low concentrations of chloride ion. For example, a solution can have a chloride ion concentration of up to and including 0.03% (w/v) (e.g., 0 to 0.03%; 0.01 to 0.03%; 0.015 to 0.03%; 0.02 to 0.03%; 0.025 to 0.03%; 0 to 0.025%; 0 to 0.2%; 0 to 0.01%; 0.005% to 0.025%; and 0.015% to 0.025%). In some embodiments, solutions having low chloride ion can be purchased commercially or may be prepared using technology known in the art, including, for example, nanofiltration, ultrafiltration, diafiltration, ion exchange chromatography, reverse osmosis, and electrolysis.

In some embodiments, a pharmaceutical composition as provided herein comprises up to and including 0.03% (w/v) of a chloride ion. In some embodiments, the chloride ion is present as a salt, for example, sodium chloride, but the chloride salt could exist in solution with other cations than sodium (e.g. hydrogen, potassium, magnesium, and calcium cations). In some embodiments, a pharmaceutical composition as provided herein comprises up to 0.03% (w/v) of a chloride ion. For example, a pharmaceutical composition comprises less than 0.03% (w/v) of a chloride ion.

In the methods described herein, the compositions provided herein (e.g., solutions of cyclodextrin, first combinations, second combinations, third combinations, and pharmaceutical compositions) have low concentrations of sodium chloride. For example, a solution can have a sodium chloride concentration of up to and including 0.05% (w/v) (e.g., 0 to 0.05%; 0.01 to 0.05%; 0.015 to 0.05%; 0.02 to 0.05%; 0.025 to 0.05%; 0.03 to 0.05%; 0.04 to 0.05%; 0 to 0.045%; 0 to 0.04%; 0 to 0.035%; 0 to 0.03%; 0 to 0.025%; 0 to 0.2%; 0 to 0.01%; 0.01% to 0.04%; 0.025% to 0.045%; and 0.02% to 0.03%). In some embodiments, solutions having low sodium chloride can be purchased commercially or may be prepared using technology known in the art, including, for example, nanofiltration, ultrafiltration, diafiltration, ion exchange chromatography, reverse osmosis, and electrolysis.

In some embodiments, a pharmaceutical composition as provided herein comprises up to and including 0.05% (w/v) of sodium chloride. In some embodiments, a pharmaceutical composition as provided herein comprises up to 0.05% (w/v) of sodium chloride. For example, a pharmaceutical composition comprises less than 0.05% (w/v) of sodium chloride.

In some embodiments, a solution of a cyclodextrin having a low concentration of any strong nucleophilic ion (e.g., chloride ion, bromide ion, fluoride ion, and iodide ion) is used to formulate a peptide proteasome inhibitor (e.g., a compound of formula (1) to (5) or a pharmaceutically acceptable salt thereof) provided herein. For example, solutions of cyclodextrins used to formulate a peptide proteasome inhibitor can have a nucleophilic ion concentration of up to and including $8.5 \times 10^{-3}$ M. Such solutions can be purchased commercially or may be prepared using technology as is known in the art. For example, nanofiltration, ultrafiltration, diafiltration, ion exchange chromatography, reverse osmosis, and electrolysis.

In some embodiments, a solution of one or more cyclodextrins used to formulate a peptide proteasome inhibitor comprises up to and including $8.5 \times 10^{-3}$ M of a nucleophilic ion. In some embodiments, the nucleophilic ion is present as a salt, for example, a sodium salt, but the nucleophilic salt could exist in solution with other cations than sodium (e.g. hydrogen, potassium, magnesium, and calcium cations). In some embodiments, a pharmaceutical composition as provided herein comprises up $8.5 \times 10^{-3}$ M of a nucleophilic ion. For example, a pharmaceutical composition comprises less than $8.5 \times 10^{-3}$ M of a nucleophilic ion.

In some embodiments, a solution of a cyclodextrin having a low concentration of chloride ion is used to formulate a peptide proteasome inhibitor (e.g., a compound of formula (1) to (5) or a pharmaceutically acceptable salt thereof) provided herein. For example, solutions of cyclodextrins used to formulate a peptide proteasome inhibitor can have a chloride ion concentration of up to and including 0.03% (w/v) (e.g., 0 to 0.03%; 0.01 to 0.03%; 0.015 to 0.03%; 0.02 to 0.03%; 0.025 to 0.03%; 0 to 0.025%; 0 to 0.2%; 0 to 0.01%; 0.005% to 0.025%; and 0.015% to 0.025%). Such solutions can be purchased commercially or may be prepared using technology as is known in the art. For example, nanofiltration, ultrafiltration, diafiltration, ion exchange chromatography, reverse osmosis, and electrolysis.

In some embodiments, a solution of one or more cyclodextrins used to formulate a peptide proteasome inhibitor comprises up to and including 0.03% (w/v) of a chloride ion. In some embodiments, the chloride ion is present as a salt, for example, sodium chloride, but the chloride salt could exist in solution with other cations than sodium (e.g. hydrogen, potassium, magnesium, and calcium cations). In some embodiments, a pharmaceutical composition as provided herein comprises up to 0.03% (w/v) of a chloride ion. For example, a pharmaceutical composition comprises less than 0.03% (w/v) of a chloride ion.

In some embodiments, a solution of a cyclodextrin having a low concentration of sodium chloride is used to formulate a peptide proteasome inhibitor (e.g., a compound of formula (1) to (5) or a pharmaceutically acceptable salt thereof) provided herein. For example, solutions of cyclodextrins used to formulate a peptide proteasome inhibitor can have a sodium chloride concentration of up to and including 0.05% (w/v) (e.g., 0 to 0.05%; 0.01 to 0.05%; 0.015 to 0.05%; 0.02 to 0.05%; 0.025 to 0.05%; 0.03 to 0.05%; 0.04 to 0.05%; 0 to 0.045%; 0 to 0.04%; 0 to 0.035%; 0 to 0.03%; 0 to 0.025%; 0 to 0.2%; 0 to 0.01%; 0.01% to 0.04%; 0.025% to 0.045%; and 0.02% to 0.03%). Such solutions can be purchased commercially or may be prepared using desalination technology as is known in the art. For example, nanofiltration, ultrafiltration, diafiltration, ion exchange chromatography, reverse osmosis, and electrolysis.

In some embodiments, a solution of one or more cyclodextrins used to formulate a peptide proteasome inhibitor comprises up to and including 0.05% (w/v) of sodium chloride. In some embodiments, a pharmaceutical composition as provided herein comprises up to 0.03% (w/v) of sodium chloride. For example, a pharmaceutical composition comprises less than 0.03% (w/v) of sodium chloride.

In addition to producing stable, highly concentrated solutions of a peptide proteasome inhibitor, the formulations prepared by the methods provided herein can be achieved without the chemical degradation and stability limitations of other methods of complexation and formulation. For example, the methods provided herein avoid the use of strong acids (e.g., HCl) to lower the pH during complexation. Although decreasing the pH of the formulation to a value less than 2 can facilitate the dissolution of the peptide proteasome inhibitor and produce a homogenous solution prior to complexation, the acidity of the solution can result in degradation of the peptide proteasome inhibitor. Moreover, the peptide proteasome inhibitor contains a ketoepoxide functional group, and the inhibitor is susceptible to hydrolysis by strong nucleophilic ions such as chloride ion. Hydrolysis of the epoxide ring and acid-catalyzed nucleophilic opening of the epoxide moiety is a route of compound degradation. For example, degradation of a compound of formula (5) results in the formation of a chlorohydrin degradation product (CDP) impurity. Based on its structure, this degradant is classified as an alkylator therefore global regulatory authorities consider this a potentially genotoxic impurity. In addition, in some embodiments, chloride ion can also degrade the epoxide resulting in formation of a chlorohydrin adduct. As shown in Example 2, reduction of chloride ion levels in a formulation of a compound of formula (5) can minimize or eliminate such hydrolysis pathways resulting in enhanced product stability and quality. Using the methods provided herein, however, such strong acids and nucleophilic ions are avoided and therefore degradation of the peptide proteasome inhibitor to such degradation products can be significantly reduced and, in some cases, may even be eliminated.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include sterile water for injection, sterile buffers, such as citrate buffer, bacteriostatic water, and Cremophor EL™ (BASF, Parsippany, N.J.). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation is freeze-drying (lyophilization), which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alia, Hamajima et al., *Clin. Immunol. Immunopathol.*, 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

The pharmaceutical compositions can be included in a container, pack, or dispenser together with instructions for administration.

Methods of Use

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations for very potent, proteasome-specific compounds, such as the epoxy ketone class of molecules, provide a means of administering a drug to a patient and treating these conditions.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these compositions are useful for treating cancer.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., *J. Mol. Med.* (1997) 75:5-17; Adams, *Nature* (2004) 4: 349-360). Therefore, provided herein is a method of treating cancers comprising administering to a patient in need of such treatment a therapeutically effective amount of a peptide proteasome inhibitor as provided herein.

As used herein, the term "cancer" includes, but is not limited to, blood born and solid tumors. Cancer refers to disease of blood, bone, organs, skin tissue and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplamacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed cellularity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous histiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

In some embodiments, a peptide proteasome inhibitor as provided herein, or a pharmaceutical composition comprising the same, can be administered to treat multiple myeloma in a patient. For example, multiple myeloma can include refractory and/or refractory multiple myeloma.

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, use of a proteasome inhibitor for the treatment of such diseases is attractive and being examined (Cilloni et al., *Haematologica* (2007) 92: 1124-1229). CMPD can include chronic myelogenous leukemia, chronic neutrophilic leukemia, chronic eosinophilic leukemia, polycythemia vera, chronic idiopathic myelofibrosis, essential thrombocythemia and unclassifiable chronic myeloproliferative disease. Provided herein is a method of treating CMPD comprising administering to a patient in need of such treatment an effective amount of the proteasome inhibitor compound disclosed herein.

Myelodisplastic/myeloproliferative diseases, such as chronic myelomonocytic leukemia, atypical chronic myeloid leukemia, juvenile myelomonocytic leukemia and unclassifiable myelodysplastic/myeloproliferative disease, are characterized by hypercellularity of the bone marrow due to proliferation in one or more of the myeloid lineages. Inhibiting the proteasome with a composition described herein, can serve to treat these myelodisplatic/myeloproliferative diseases by providing a patient in need of such treatment an effective amount of the composition.

Myelodysplastic syndromes (MDS) refer to a group of hematopoietic stem cell disorders characterized by dysplasia and ineffective haematopoiesis in one or more of the major myeloid cell lines. Targeting NF-kB with a proteasome inhibitor in these hematologic malignancies induces apoptosis, thereby killing the malignant cell (Braun et al. *Cell Death and Differentiation* (2006) 13:748-758). Further provided herein is a method to treat MDS comprising administering to a patient in need of such treatment an effective amount of a compound provided herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del (5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extracutaneous mastocytoma. Further provided herein is a method to treat mastocytosis comprising administering an effect amount of the compound disclosed herein to a patient diagnosed with mastocytosis.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Thus, provided herein are methods of affecting the level of expression of IL-2, MHC-I, IL-6, TNFα, IFN-β or any of the other previously-mentioned proteins, each method comprising administering to a patient an effective amount of a proteasome inhibitor composition disclosed herein.

Also provided herein is a method of treating an autoimmune disease in a patient comprising administering a therapeutically effective amount of the compound described herein. An "autoimmune disease" herein is a disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiffman syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation or present unfamiliar peptides on their surface. Intracellular proteolysis generate small peptides for presentation to T-lymphocytes to induce MHC class I-mediated immune responses. Thus, provided herein is a method of using a proteasome inhibitor provided herein as an immunomodulatory agent for inhibiting or altering antigen presentation in a cell, comprising exposing the cell (or administering to a patient) to the compound described herein. Specific embodiments include a method of treating graft or transplant-related diseases, such as graft-versus-host disease or host versusgraft disease in a patient, comprising administering a therapeutically effective amount of the compound described herein. The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same patient. In some embodiments, the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. *Cancer Res.* (2006) 66:5461-5468). In some embodiments, a composition provided herein can be administered to a patient with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor and non-specified dendritic cell sarcoma.

Inhibition of the proteasome has been shown to be beneficial to treat diseases whereby a cell type is proliferating and immune disorders; thus, in some embodiments, the treatment of lymphoproliferative diseases (LPD) associated with primary immune disorders (PID) is provided comprising administering an effective amount of the disclosed compound to a patient in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in patients who have received solid organ or bone marrow allografts, and iatrogenis immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Proteasome inhibition has also been associated with inhibition of NF-κB activation and stabilization of p53 levels. Thus, compositions provided herein may also be used to inhibit NF-κB activation, and stabilize p53 levels in cell culture. Since NF-κB is a key regulator of inflammation, it is an attractive target for anti-inflammatory therapeutic intervention. Thus, compositions provided herein may be useful for the treatment of conditions associated with inflammation, including, but not limited to COPD, psoriasis, asthma, bronchitis, emphysema, and cystic fibrosis.

The disclosed compositions can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

In some embodiments, a composition provided herein is useful for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three iso forms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser (SEQ ID NO:1), which is identical to the β-subunit of human macropain (Kojima, S. et al., Fed. Eur. Biochem. Soc, (1992) 304:57-60). The APP-processing enzyme cleaves at the Gin 15-Lysl 6 bond; in the presence of calcium ion, the enzyme also cleaves at the Met-1-Asp 1 bond, and the Asp1-Ala2 bonds to release the extracellular domain of β-AP.

One embodiment, therefore, is a method of treating Alzheimer's disease, including administering to a patient an effective amount of a composition provided herein. Such treatment includes reducing the rate of β-AP processing, reducing the rate of β-AP plaque formation, reducing the rate of β-AP generation, and reducing the clinical signs of Alzheimer's disease.

Also provided herein are methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Peptide proteasome inhibitors as provided herein are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736. Methods of treatment include: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a patient) with an effective amount of a pharmaceutical composition disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity. However, accelerated degradation of the TGF-β signaling components has been observed in cancers and other hyperproliferative conditions. Thus, in certain embodiments, a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders) is provided. The treatment of burn victims is often hampered by fibrosis, thus, in some embodiments an inhibitor provided herein may be administered by topical or systemic administration to treat burns. Wound closure following surgery is often associated with disfiguring scars, which may be prevented by inhibition of fibrosis. Thus, in certain embodiments, a method for the prevention or reduction of scarring is provided herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., *Cell* (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain x gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Some embodiments include methods of affecting the level of expression of IL-2, MHC-I, IL-6, TNFα, IFN-β, or any of the other previously-mentioned proteins, each method including administering to a patient an effective amount of a composition disclosed herein. Complexes including p50 are rapid mediators of acute inflammatory and immune responses (Thanos, D. and Maniatis, T., *Cell* (1995) 80:529-532).

NF-κB also participates in the expression of the cell adhesion genes that encode E-selectin, P-selectin, ICAM, and VCAM-1 (Collins, T., Lab. *Invest.* (1993) 68:499-508). In some embodiments, a method for inhibiting cell adhesion (e.g., cell adhesion mediated by E-selectin, P-selectin, ICAM, or VCAM-1) is provided, including contacting a cell with (or administering to a patient) an effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Thus, provided herein is a method of treating an ischemic condition or reperfusion injury comprising administering to a patient in need of such treatment an effective amount of a compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., Science, (1995) 267:960). Provided herein is a method for inhibiting or reducing HIV infection in a patient, and a method for decreasing the level of viral gene expression, each method including administering to the patient an effective amount of a composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronavirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, a method for treating viral infection, such as SARS or hepatitis A, B, C, D and E, is provided comprising contacting a cell with (or administering to a patient) an effective amount of the compound disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., J. Immun. (2003) 171: 1515-1525). Therefore, in certain embodiments, compositions as provided herein may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. A further embodiment is a method for suppressing the immune system of a patient (e.g., inhibiting transplant rejection, allergy, asthma), including administering to the patient an effective amount of a composition described herein. Compositions provided herein can also be used to treat autoimmune diseases such as lupus, rheumatoid arthritis, multiple sclerosis, and inflammatory bowel diseases such as ulcerative colitis and Crohn's disease.

Another embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. Cell (1994) 78:773-785; and Traenckner, et al., EMBO J. (1994) 13:5433-5441). In some embodiments, a method for inhibiting IκB-α degradation is provided, including contacting the cell with a composition described herein. A further embodiment is a method for reducing the cellular content of NF-κB in a cell, muscle, organ, or patient, including contacting the cell, muscle, organ, or patient with a composition described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Further provided herein are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAAL-GNISEN-50 (SEQ ID NO: 2) (destruction box). There is evidence that cyclin is converted to a form vulnerable to a ubiquitin ligase or that a cyclin-specific ligase is activated during mitosis (Ciechanover, A., Cell, (1994) 79: 13-21). Inhibition of the proteasome inhibits cyclin degradation, and therefore inhibits cell proliferation, for example, in cyclin-related cancers (Kumatori et al., Proc. Natl. Acad Sci. USA (1990) 87:7071-7075). Provided herein is a method for treating a proliferative disease in a patient (e.g., cancer, psoriasis, or restenosis), including administering to the patient an effective amount of a composition disclosed herein. Also provided herein is a method for treating cyclin-related inflammation in a patient, including administering to a patient a therapeutically effective amount of a composition described herein.

Additional embodiments include methods for affecting the proteasome-dependent regulation of oncoproteins and methods of treating or inhibiting cancer growth, each method including exposing a cell (in vivo, e.g., in a patient, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a patient an effective amount of a composition disclosed herein.

In another embodiment, the disclosed compositions are useful for the treatment of a parasitic infection, such as infections caused by protozoan parasites. The proteasome of these parasites is considered to be involved primarily in cell differentiation and replication activities (Paugam et al., *Trends Parasitol.* 2003, 19(2): 55-59). Furthermore, entamoeba species have been shown to lose encystation capacity when exposed to proteasome inhibitors (Gonzales, et al., *Arch. Med. Res.* 1997, 28, Spec No: 139-140). In certain such embodiments, the disclosed compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds useful as proteasome inhibitors in the treatment of parasitic diseases are described in WO 98/10779, which is incorporated herein in its entirety.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. In some embodiments, a method of treating prokaryotic infections is provided, comprising administering to a patient an effective amount of the proteasome inhibitor composition disclosed herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteoporosis.

Provided herein is a method for treating a disease or condition selected from cancer, autoimmune disease, graft or transplant-related condition, neurodegenerative disease, fibrotic-associated condition, ischemic-related conditions, infection (viral, parasitic or prokaryotic) and diseases associated with bone loss, comprising administering a proteasome inhibitor as provided herein. For example, a compound of formula (5).

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, compounds provided herein may also be useful for hair follicle growth stimulation.

Finally, the disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process. Administration Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent in addition to a cyclodextrin and a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect. In general, compositions intended for parenteral use (e.g., intravenous, subcutaneous injection) include a substituted cyclodextrin. Compositions administered via other routes, particularly the oral route, include a substituted or unsubstituted cyclodextrin.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified peptide proteasome inhibitor in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, the peptide proteasome inhibitors provided herein may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A peptide proteasome inhibitor can be administered by aerosol. This is accomplished by preparing an aqueous aerosol, liposomal preparation, or solid particles containing the composition. A nonaqueous (e.g., fluorocarbon propellant) suspension could be used. In some embodiments, sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions suitable for parenteral administration comprise one or more peptide proteasome inhibitors in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), ethanol, polyols (such as glycerol, propylene glycol, polyethylene glycol, and the like), buffer (such as citrate buffer), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Pharmaceutical compositions typically include a pharmaceutically acceptable carrier. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. In some embodiments, a pharmaceutically acceptable carrier is a buffer (e.g., citrate buffer). In some embodiments, a pharmaceutically acceptable carrier is sterile water for injection. In some embodiments, a pharmaceutically acceptable carrier comprises citric acid.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

The peptide proteasome inhibitors described herein may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, a peptide proteasome inhibitor, which may be used in a suitable hydrated form, and/or the pharmaceutical compositions provided herein, is formulated into a pharmaceutically acceptable dosage form by conventional methods known to those of skill in the art.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions provided herein may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds. The dosage will be an effective amount depending on several factors including the overall health of a patient, and the formulation and route of administration of the selected compound(s).

In another embodiment, the pharmaceutical composition is an oral solution or a parenteral solution. Another embodiment is a freeze-dried preparation that can be reconstituted prior to administration. As a solid, this formulation may also include tablets, capsules or powders.

Also provided herein is a conjoint therapy wherein one or more other therapeutic agents are administered with a peptide proteasome inhibitor or a pharmaceutical composition comprising a peptide proteasome inhibitor. Such conjoint treatment may be achieved by way of the simultaneous, sequential, or separate dosing of the individual components of the treatment.

In certain embodiments, a composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more other proteasome inhibitor(s).

In certain embodiments, a composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more chemotherapeutics. Suitable chemotherapeutics may include, natural products such as vinca alkaloids (i.e. vinblastine, vincristine, and vinorelbine), taxanes (e.g., docetaxel, paclitaxel, e.g., docetaxel), epipodophyllotoxins (i.e. etoposide, teniposide), antibiotics (dactinomycin (actinomycin D) daunorubicin, doxorubicin and idarubicin; e.g., doxorubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, ifosfamide, cyclophosphamide and analogs, melphalan, chlorambucil, e.g., melphalan), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); platinum coordination complexes (cisplatin, carboplatin), procarbazine, hydroxyurea, mitotane, aminoglutethimide; DNA binding/Cytotoxic agents (e.g., Zalypsis); histone deacetylase (HDAC) inhibitors (e.g., trichostatin, sodium butyrate, apicidan, suberoyl anilide hydroamic acid (SAHA (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxy-carbonyl)aminomethyl]benzamide), LAQ824/LBH589, CI994, MGCD0103, ACY-1215, Panobinostat); hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a pharmaceutical composition as provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more histone deacetylase (HDAC) inhibitors (e.g., trichostatin, sodium butyrate, apicidan, suberoyl anilide hydroamic acid ("SAHA" (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxy-carbonyl)aminomethyl]benzamide), LAQ824/LBH589, CI994, MGCD0103, ACY-1215, Panobinostat; e.g., SAHA, ACY-1215, Panobinostat).

In certain embodiments, a pharmaceutical composition as provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more nitrogen mustards (mechlorethamine, ifosphamide, cyclophosphamide and analogs, melphalan, chlorambucil, e.g., melphalan).

In certain embodiments, a pharmaceutical composition as provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more DNA binding/Cytotoxic agents (e.g., Zalypsis).

In certain embodiments, a pharmaceutical composition as provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more taxanes (e.g., docetaxel, paclitaxel, e.g., docetaxel).

In certain embodiments, a pharmaceutical composition as provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more antibiotics (dactinomycin (actinomycin D) daunorubicin, doxorubicin and idarubicin; e.g., doxorubicin).

In some embodiments, a pharmaceutical composition as provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more cytokines. Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more steroids. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof (e.g., hydrocortisone, dexamethasone, methylprednisolone and prednisolone; e.g., dexamethasone).

In certain embodiments, pharmaceutical compositions provided herein are conjointly administered with dexamethasone (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)). In certain embodiments, conjoint therapy includes the dosing regimens provided on the KYPROLIS label, e.g., 1. KYPROLIS is administered intravenously over 2 to 10 minutes, on two consecutive days, each week for three weeks (Days 1, 2, 8, 9, 15, and 16), followed by a 12-day rest period (Days 17 to 28). Each 28-day period is considered one treatment cycle (Table A).

In Cycle 1, KYPROLIS is administered at a dose of 20 mg/m². If tolerated in Cycle 1, the dose should be escalated to 27 mg/m² beginning in Cycle 2 and continued at 27 mg/m² in subsequent cycles. Treatment may be continued until disease progression or until unacceptable toxicity occurs.

The dose is calculated using the patient's actual body surface area at baseline. Patients with a body surface area greater than 2.2 m² should receive a dose based upon a body surface area of 2.2 m². Dose adjustments do not need to be made for weight changes of less than or equal to 20%.

TABLE A1

KYPROLIS Dosage Regimen for Patients with Multiple Myeloma

| | Week 1 | | | Week 2 | | | Week 3 | | | Week 4 |
|---|---|---|---|---|---|---|---|---|---|---|
| | Day 1 | Day 2 | Days 3-7 | Day 8 | Day 9 | Days 10-14 | Day 15 | Day 16 | Days 17-21 | Days 22-28 |
| | | | | | Cycle 1 | | | | | |
| KYPROLIS (20 mg/m²): | 20 | 20 | No Dosing | 20 | 20 | No Dosing | 20 | 20 | No Dosing | No Dosing |
| | | | | | Cycles 2 and Beyond[a] | | | | | |
| KYPROLIS (27 mg/m²): | 27 | 27 | No Dosing | 27 | 27 | No Dosing | 27 | 27 | No Dosing | No Dosing |

[a] If previous cycle dosage is tolerated.

2. Hydrate patients to reduce the risk of renal toxicity and of tumor lysis syndrome (TLS) with KYPROLIS treatment. Maintain adequate fluid volume status throughout treatment and monitor blood chemistries closely. Prior to each dose in Cycle 1, give 250 mL to 500 mL of intravenous normal saline or other appropriate intravenous fluid. Give an additional 250 mL to 500 mL of intravenous fluids as needed following KYPROLIS administration. Continue intravenous hydration, as needed, in subsequent cycles. Also monitor patients during this period for fluid overload.

3. Pre-medicate with dexamethasone 4 mg orally or intravenously prior to all doses of KYPROLIS during Cycle 1 and prior to all KYPROLIS doses during the first cycle of dose escalation to 27 mg/m² to reduce the incidence and severity of infusion reactions. Reinstate dexamethasone premedication (4 mg orally or intravenously) if these symptoms develop or reappear during subsequent cycles.

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more immunotherapeutic agents. Suitable immunotherapeutic agents may include, but are not limited to, MDR modulators (verapamil, valspordar, biricodar, tariquidar, laniquidar), cyclosporine, pomalidomide, thalidomide, CC-4047 (Actimid), lenalidomide (Revlimid) and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab. In certain embodiments, a pharmaceutical composition provided herein is conjointly administered with lenalidomide (Revlimid).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more topoisomerase inhibitors (e.g., irinotecan, topotecan, camptothecin, lamellarin D, and etoposide).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more m-TOR inhibitors (e.g., CCI-779, AP23573 and RAD-001).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more protein kinase inhibitors (e.g., sorafenib, imatinib, dasatinib, sunitinib, pazopanib, and nilotinib; e.g., sorafenib).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more CDK Inhibitors (e.g., Dinaciclib).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more KSP(Eg5) Inhibitors (e.g., Array 520).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more PI13 delta Inhibitors (e.g., GS-1101 PI3K).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more Dual Inhibitor: PI3K delta and gamma Inhibitors (e.g., CAL-130).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more multi-kinase Inhibitors (e.g., TG02).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with one or more PI3K delta Inhibitors (e.g., TGR-1202).

In some embodiments, a pharmaceutical composition provided herein (e.g., pharmaceutical compositions that include carfilzomib, e.g, KYPROLIS, which contains 60 mg of carfilzomib, 3000 mg sulfobutylether beta-cyclodextrin, 57.7 mg citric acid, and sodium hydroxide for pH adjustment (target pH 3.5)) is conjointly administered with
  (i) one or more of the following:
    one or more second chemotherapeutic agents (e.g., one or more HDAC inhibitors, e.g., SAHA, ACY-1215, Panobinostat; one or more nitrogen mustards e.g., melphalan; one or more DNA binding/cytotoxic agents, e.g., Zylapsis; one or more taxanes, e.g., docetaxel; one or more antibiotics (dactinomycin (actinomycin D) daunorubicin, doxorubicin and idarubicin; e.g., doxorubicin);
    one or more other proteasome inhibitor(s) (e.g., another compound of formulae (1)-(5));
    one or more cytokines;
    one or more immunotherapeutic agents (e.g., Revlimid);
    one or more topoisomerase inhibitors;
    one or more m-TOR inhibitors;
    one or more protein kinase inhibitors (e.g., sorafenib);
    one or more CDK Inhibitors (e.g., Dinaciclib);
    one or more KSP(Eg5) Inhibitors (e.g., Array 520);
    one or more PI13 delta Inhibitors (e.g., GS-1101 PI3K);
    one or more Dual Inhibitor: PI3K delta and gamma Inhibitors (e.g., CAL-130);
    one or more multi-kinase Inhibitors (e.g., TG02);
    one or more PI3K delta Inhibitors (e.g., TGR-1202);
    and
  (ii) one or more steroids (e.g., dexamethasone).

In certain embodiments, a pharmaceutical composition that includes carfilzomib (e.g, KYPROLIS, which contains 60 mg of carfilzomib, 3000 mg sulfobutylether beta-cyclodextrin, 57.7 mg citric acid, and sodium hydroxide for pH adjustment (target pH 3.5) is conjointly administered with
  (i) one of the following:
    one or more second chemotherapeutic agents (e.g., one or more HDAC inhibitors, e.g., SAHA, ACY-1215, Panobinostat; one or more nitrogen mustards e.g., melphalan; one or more DNA binding/cytotoxic agents, e.g., Zylapsis; one or more taxanes, e.g., docetaxel; one or more antibiotics (dactinomycin (actinomycin D) daunorubicin, doxorubicin and idarubicin; e.g., doxorubicin);
    one or more other proteasome inhibitor(s) (e.g., another compound of formulae (1)-(5));
    one or more cytokines;
    one or more immunotherapeutic agents (e.g., Revlimid);
    one or more topoisomerase inhibitors;
    one or more m-TOR inhibitors;
    one or more protein kinase inhibitors (e.g., sorafenib);
    one or more CDK Inhibitors (e.g., Dinaciclib);
    one or more KSP(Eg5) Inhibitors (e.g., Array 520);
    one or more PI13 delta Inhibitors (e.g., GS-1101 PI3K);
    one or more Dual Inhibitor: PI3K delta and gamma Inhibitors (e.g., CAL-130);
    one or more multi-kinase Inhibitors (e.g., TG02);
    one or more PI3K delta Inhibitors (e.g., TGR-1202);
    and
  (ii) dexamethasone.

EXAMPLES

Example 1. Preparation of a Suspension of Carfilzomib-Active Pharmaceutical Ingredient (CFZ-API) in Sulfobutylether Beta-Cyclodextrin (SBECD)

This Example describes the preparation of a suspension of CFZ-API in SBECD at 400 L batch size. Smaller batch sizes were performed in equivalent proportions of the constituents, such as at 290 L, 90 L, and 1-3 L batch sizes.

In a 525 L stainless steel jacketed cooled tank controlled to 2° C.-8° C., a suspension of 2.0 kg carfilzomib-API (CFZ-API), 246 kg water for injection (WFI), and 100 kg sulfobutylether beta-cyclodextrin (SBECD) was prepared. Specifically, in the 525 L stainless steel jacketed cooled tank controlled to 2° C.-8° C., 100 kg SBECD was dissolved in 246 kg WFI. The Carfilzomib suspension was then prepared using 2.0 kg of CFZ-API. Mixing was performed using an impeller mixer to maintain suspension of the CFZ-API solids and dissolve the SBECD. In the same vessel, a probe style rotor-stator high shear mixer (homogenizer) was used as well as the low shear impeller. The high shear mixer was operated for approximately 1 hour yielding an even suspension and reduction of particle size for any larger primary particles or agglomerated API. After a suspension was achieved, 1.96 kg of citric acid was added as a 16% aqueous solution. The pH of the solution was then lowered inducing partial solubilization of the CFZ-API followed by and complexation due to the presence of SBECD. Mixing was continued for a further 24 hours with both the impeller and the high shear mixer and a dissolved concentration of CFZ-API of greater than 5.1 mg/mL was achieved. The suspension containing greater than 5.1 mg/mL of dissolved complexed CFZ-API was filtered with a 0.45 micrometer clarifying filter, then accurately diluted to a dissolved concentration of 5.0 mg/mL and pH adjusted with 1 N sodium hydroxide solution to achieve pH 3.5. The solution was sterile filtered, with two sequential 0.22 micrometer sterilizing filters, then filled into vials 12.36 mL each, containing 61.8 mg per vial of CFZ-API. The vials were partially stoppered and loaded into a lyophilizer and freeze dried over 103 hours using a freezing temperature of −45° C., primary drying temperature of −15° C., and secondary drying of +30° C. The lyophilized vials were fully stoppered, and capped, then stored at the product stability temperature of 2° C.-8° C. for up to two years before use. Upon use, the vial was reconstituted with sterile water for injection to yield a 2 mg/mL reconstituted solution for injection, having pH 3.5 and tonicity acceptable for direct injection into patients. Alternately, the reconstituted solution was further diluted in an intravenous bag for further dilution and infusion without inducing precipitation.

Figure 2:
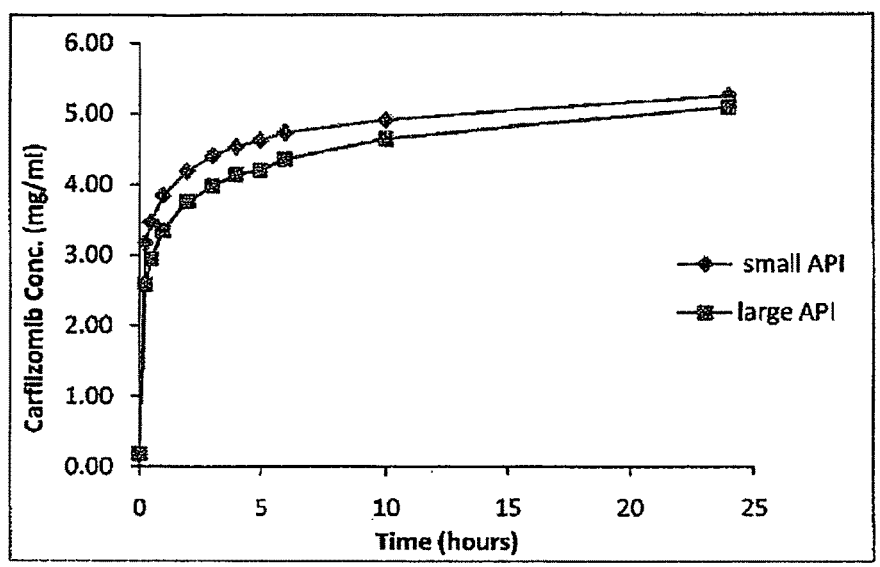
FIG. 2 illustrates the independence of the pharmaceutical compositions prepared herein on physiochemical properties (e.g., particle size) of the proteasome inhibitor.
Figure 3:
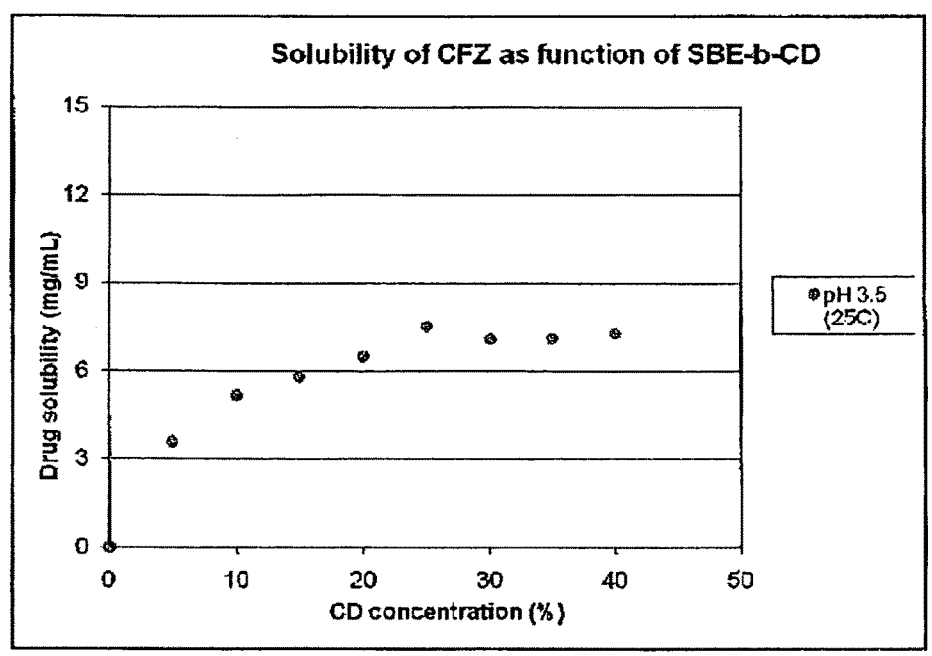
FIG. 3 is a line graph showing an increase in CFZ-API solubilization with increasing SBECD concentration.
Figure 4:
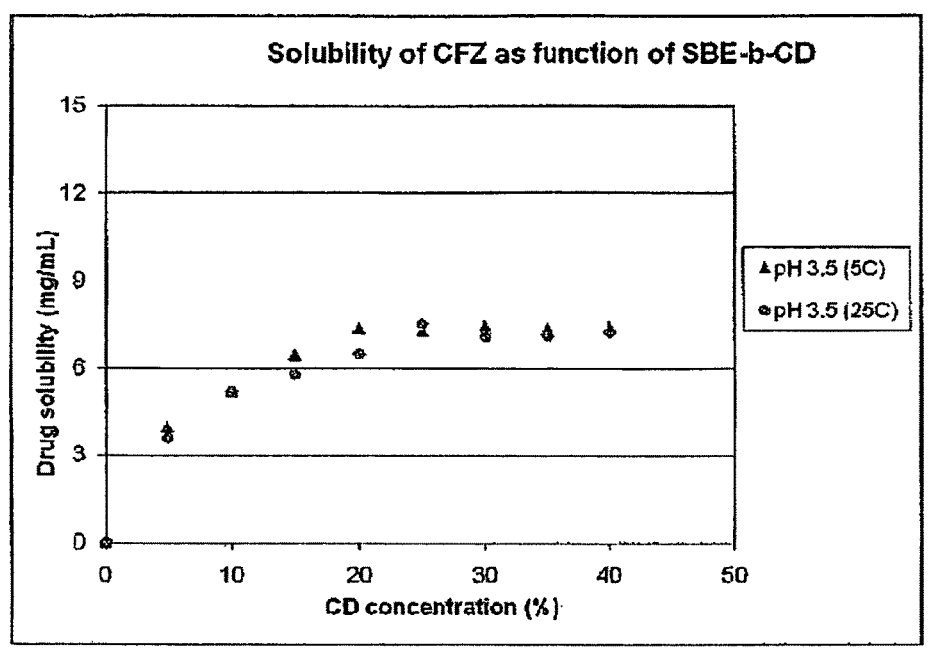
FIG. 4 illustrates the independence of CFZ-API/SBECD complex solubility on processing or storage temperature.

As shown in FIG. 1, the slurry based process of complexation results in increased solubilization of the CFZ-API over time (greater than 5 milligrams per milliliter, which is substantially higher than the intrinsic aqueous solubility of CFZ-API, which is less than 10 micrograms per milliliter). In addition, the process is less dependent on the physicochemical properties of the CFZ-API (e.g., particle size, surface area, degree of agglomeration, polymorphic form, etc.). Unlike most pharmaceutical production or testing, dissolution rate (or solubilization rate) in this process is effectively independent on the particle size of the API (see, e.g., FIG. 2) as the process delivers an equivalent extent of solubilization over the 24 hour period of time for complexation to occur regardless of whether the API initially had a large or small mean API particle size (21.1 micrometers, and 7.5 micrometers respectively). It was further determined that in the process described above, higher concentrations of SBECD increased the solubility of the CFZ-API (see FIG. 3). Finally, it has been observed that the complexed solubility of CFZ/SBECD was effectively independent of processing or storage temperature (see, e.g., FIG. 4 where solubilized extent is shown as a function of SBECD concentration at pH 3.5 for two temperatures 5° C. and 25° C. showing no apparent difference). Therefore lower processing temperatures are preferred (2° C.-8° C.) to minimize potential for any thermally induced degradation reactions that may occur. In other processes, more commonly higher temperatures are necessary to increase solubility, however in this process, higher solubility is achieved via increasing cyclodextrin concentration and/or pH rather than by increasing temperature and this enables thermal degradants to be minimized in this process.

Example 2. Effect of Chloride Ion on the Stability of Carfilzomib

A multivariate statistical design of experiments was conducted to assess factors controlling the level of chlorohydrin degradation product as a function of processing parameters and storage time over six months. The complexation was performed in the proportion and parameters given in Example 1, with the following modifications: (i) the complexation process was performed at 2 L batch size; (ii) the final pH of solution before vial filling was varied for purposes of the experiment from 3.0, to 4.0; (iii) sodium chloride was spiked into SBECD in some experiments to create a high sodium chloride condition; (iv) water content of the lyophilized final product in stoppered vials was produced at high and low sodium chloride conditions via early termination and stoppering of vials to create a higher residual water content condition.
Materials.

TABLE 2

| Materials | |
|---|---|
| Item | Manufacturer |
| Carfilzomib drug substance | Cambridge Major Laboratories |
| Citric acid, anhydrous | J. T. Baker |

TABLE 2-continued

| Materials | |
|---|---|
| Item | Manufacturer |
| Sulfobutylether-β-cyclodextrin (Captisol ®) | CyDex Pharmaceuticals, Inc. |
| Sodium Chloride | EMD Chemicals, Inc. |
| Water for Injection (WFI) | EMD Chemicals, Inc. |
| Sodium Hydroxide solution 1.000N | EMD Chemicals, Inc. |
| Overhead Mixer (impeller, low shear) | IKA Works |
| Impeller | NA |
| High Shear Mixer | Silverson |
| Recirculating Water Bath | Thermo Electron Corp |
| 50 mL 20 mm molded glass, 20 mm single-vent flurotech stoppers | Wheaton West Pharma |
| Genesis SQ 35 EL Freeze-Dryer | VirTis |
| 0.22 µm syringe driven filter | Millipore |
| 0.22 µm PES filter system | Corning |
| pH meter | Beckman |
| pH electrode | Orion ROSS |
| pH 1.68 buffer | ThermoElectron Corp. |
| pH 4.0 buffer | VWR |

Methods.
Complexation Process:
The solution of complexed carfilzomib for injection bulk solution pre-lyophilization included aqueous 5 mg/mL carfilzomib, 250 mg/mL Captisol® (SBECD) and 4.86 mg/mL citric acid, pH adjusted with aqueous sodium hydroxide. Compounding of the bulk solutions for lyophilization followed the procedure detailed in Example 1 with the following manipulations to create solutions with different specific attributes:
  1. pH was adjusted to 3.0 and 4.0
  2. Sodium chloride was spiked into the Captisol® to create a "High Chloride" condition Captisol® manufactured by Cydex, a subsidiary of Ligand, has a standard product analysis range for sodium chloride from 0.05% to 0.2% (w/v). One lot of Captisol® was available for experimentation which had a low chloride content of only 0.05% (w/v) as sodium chloride. 400 g of this Captisol® was required per batch for the process to be performed at 2 L scale batches of complexation processing (in same proportions and general parameters per Example 1). To create the "high chloride" condition, 0.6 g of NaCl was added to 399.4 g of Captisol® which thus mimicked what a batch containing 0.2% chloride Captisol® would be comprised of.

Lyophilization:
In order to generate two (2) moisture content conditions in the final lyophilized vials, two (2) sets of 61.8 mg/vial (of CFZ-API) samples were lyophilized. The first cycle generated the "dry" sample set of vials containing approximately 0.6% residual water per Example 1 lyophilization parameters. For the second sample set, lyophilization was terminated and vials stoppered earlier in the secondary drying phase to generate the "wet" condition vials, with residual moisture approximately 2.4% water per vial initially.

One (1) lot of placebo was prepared as a control containing 250 mg/mL Captisol® and 4.86 mg/mL citric acid, adjusted to pH 3.5 with NaOH.

Analytical Testing:
The bulk solution of complexed carfilzomib was analyzed during manufacture by High Performance Liquid Chromatography (HPLC) to accurately quantify the concentration of dissolved and complexed carfilzomib drug substance. Subsequently, additional water was added to accurately dilute the bulk complexed solution. After this dilution step, HPLC was used again to ensure a target concentration of 5.0 mg/mL was achieved. Samples of the three (3) final bulk solutions were analyzed for potency and purity confirmation testing by HPLC. Stability samples were analyzed after six months of storage at 5° C. and 25° C. by HPLC for potency and purity. Karl Fischer Coulometry method was used for the water content determination in the lyophilized drug product.

Data Treatment:
Stat-Ease DX7 was used to analyze the results.
Results.
The results for formation of a chlorohydrin degradation product (CDP) at 6 months for 5° C. and 25° C. are summarized in Table 3 below.

TABLE 3

Results for CDP formation after 6 months at 5° C. and 25° C.

| pH | Water (%) | Sodium Chloride (%) | % Area of CDP after 6 months (HPLC data) | |
|---|---|---|---|---|
| | | | 5° C. | 25° C. |
| 4.00 | 2 | 0.05 | 0.02 | 0.35 |
| 3.00 | 2 | 0.05 | 0.02 | 0.55 |
| 3.00 | 0.7 | 0.05 | 0.00 | 0.14 |
| 4.00 | 0.7 | 0.05 | 0.00 | 0.09 |
| 4.00 | 2 | 0.2 | 0.18 | 1.71 |
| 3.00 | 2 | 0.2 | 0.28 | 2.57 |
| 4.00 | 0.7 | 0.2 | 0.08 | 0.36 |
| 3.00 | 0.7 | 0.2 | 0.13 | 0.70 |

Figure 5:
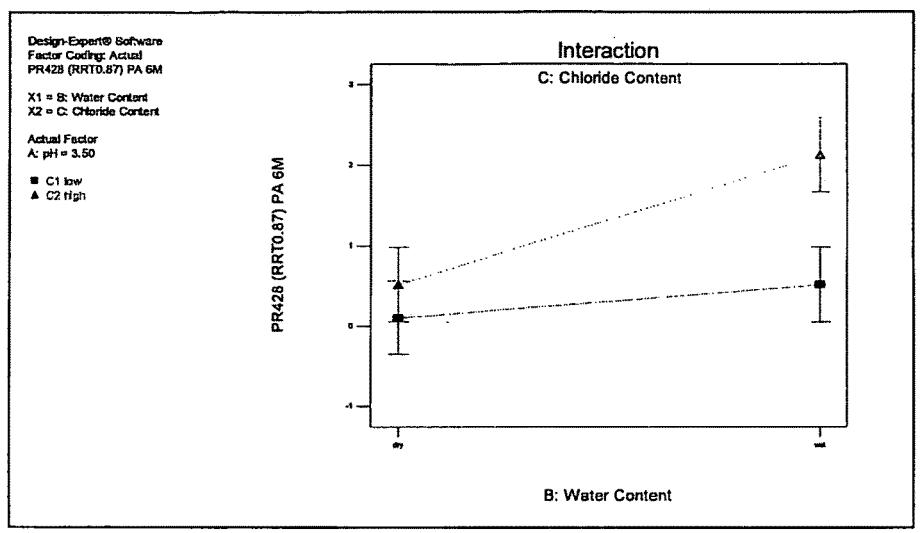
FIG. 5 illustrates the correlation between the levels of chlorohydrin degradation product (CDP) and the two-factor interaction of water and chloride content at pH 3.5.

The ANOVA analyses below (Table 4 and 5) for CDP shows that chloride content is the main factor in CDP formation. Higher chloride content leads to greater levels of the CDP. Even at the low level of chloride content (0.05% (w/v)), formation of the chlorohydrin is still observed but at acceptably low concentration compared to 0.2% chloride. In addition, drug product containing low levels of chloride ion showed unacceptable formation of chlorohydrin product at 25° C. after 6 months of storage. FIG. 5 illustrates the relationship between CDP and the two-factor interaction of water and chloride content. The top line is high chloride content and the bottom line is low chloride content. The x-axis represents water content, with 0.7% on the left and 2% on the right. At higher chloride levels, the levels of CDP production increases. This increase is more even more evident at higher water content conditions, as can be seen from the slope of the top curve. At low chloride levels, there is little difference seen between low or high water content conditions.

TABLE 4

ANOVA analysis - CDP (RRT 0.86) at 6 Months, 5° C.
Response 1 CDP (RRT0.87) PA 6 M 5 C.
ANOVA for selected factorial model
Analysis of variance table [Partial sum of squares - Type III]

| Source | Sum of Squares | df | Mean Square | F Value | p-value Prob > F | |
|---|---|---|---|---|---|---|
| Model | 0.028 | 1 | 0.028 | 6.88 | 0.0394 | significant |
| C-Chloride Content | 0.028 | 1 | 0.028 | 6.88 | 0.0394 | |
| Residual | 0.024 | 6 | 4.013E−003 | | | |
| Cor Total | 0.052 | 7 | | | | |

TABLE 5

ANOVA analysis - CDP (RRT 0.86) at 6 Months, 25° C.
Response 1 CDP (RRT0.87) PA 6 M 25 C.
ANOVA for selected factorial model
Analysis of variance table [Partial sum of squares - Type III]

| Source | Sum of Squares | df | Mean Square | F Value | p-value Prob > F | |
|---|---|---|---|---|---|---|
| Model | 4.81 | 3 | 1.60 | 14.42 | 0.0130 | significant |
| B-Water Content | 2.05 | 1 | 2.05 | 18.43 | 0.0127 | |
| C-Chloride Content | 2.05 | 1 | 2.05 | 18.43 | 0.0127 | |
| BC | 0.71 | 1 | 0.71 | 6.42 | 0.0644 | |
| Residual | 0.45 | 4 | 0.11 | | | |
| Cor Total | 5.26 | 7 | | | | |

Example 3. Effect of Hydrochloric and Citric Acids on Chlorohydrins Degradation Product A study was conducted to determine the impact of using hydrochloric acid in the complexation process by comparing the impurity levels of degradation product CDP over storage time to lot produced without HCl, and stored for the same period of time. During production, the pH of all lots was adjusted at the end of the process to 3.5 using sodium hydroxide.

As presented in Table 6, lots produced with the addition of HCl (2, 3, and 4) showed a clear formation of the chlorohydrin degradation product (CDP) over the course of storage time, whereas at the recommended storage temperature of 5° C., CDP was mostly below the HPLC reporting limit (0.1%) or not detected (ND) in lots 1 and 5 (where no HCl was used). Clearly, more chloride content coming from HCl as the acid for initiating complexation resulted in more (and unacceptable levels of) CDP formation. Therefore, using the weaker acid citric acid alone to initiate complexation in SBECD minimized CDP formation.

TABLE 6

Results for CDP formation (% Area) at 5° C. and 25° C.

| Time (month) | Lot 1 Citric acid (no HCl) | | Lot 2 Hydrochloric acid | | Lot 3 Hydrochloric acid | | Lot 4 Hydrochloric acid | | Lot 5 Citric acid (no HCl) | |
|---|---|---|---|---|---|---|---|---|---|---|
| | 5° C. | 25° C. | 5° C. | 25° C. | 5° C. | 25° C. | 5° C. | 25° C. | 5° C. | 25° C. |
| 0 | ≤0.1 | ND | 0.16 | 0.16 | 0.26 | 0.26 | 0.15 | 0.15 | ≤0.1 | ≤0.1 |
| 3 | ≤0.1 | 0.13 | 0.24 | 0.78 | 0.36 | 1.4 | 0.19 | 0.78 | ≤0.1 | 0.19 |
| 6 | ≤0.1 | ≤0.1 | 0.26 | 1.1 | 0.37 | 1.9 | 0.22 | 1.1 | ≤0.1 | 0.31 |
| 12 | ≤0.1 | — | 0.24 | — | 0.46 | — | 0.25 | — | ≤0.1 | — |
| 18 | ≤0.1 | — | 0.35 | — | 0.52 | — | 0.29 | — | ≤0.1 | — |
| 24 | ≤0.1 | — | 0.33 | — | 0.64 | — | 0.32 | — | 0.12 | — |

Example 4

Figure 6:
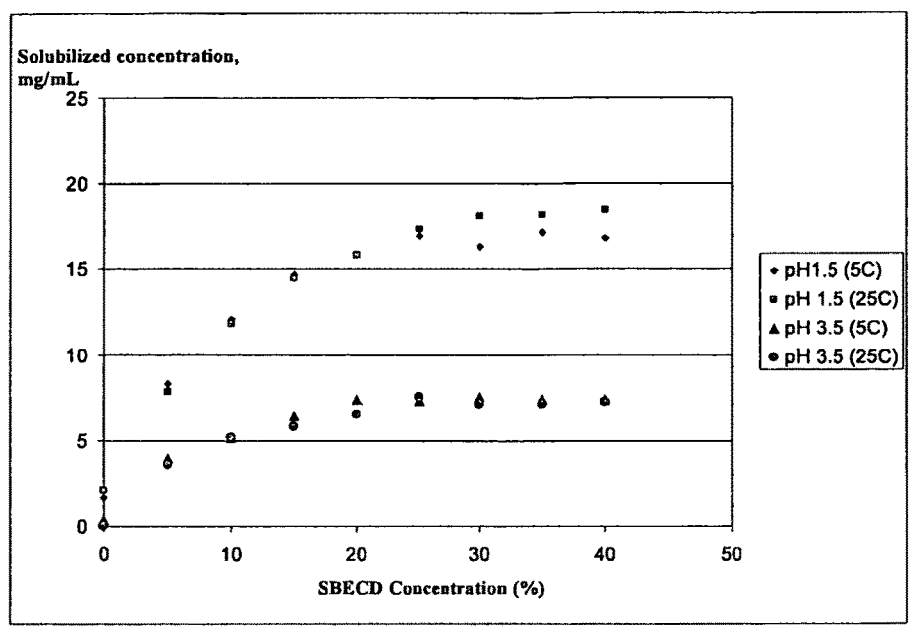
FIG. 6 illustrates carfilzomib solubility in SBECD at pH 1.5 and pH 3.5, 25° C. and 5° C., (5.9 mg/mL Citric Acid).

The solubility of carfilzomib as a function of SBECD cyclodextrin concentration was determined in aqueous solutions containing citric acid (30 mM), at pH 1.5 and pH 3.5, and at temperatures including 5° C. and 25° C. The solubility profile is shown in FIG. 6. No significant differences in solubility were observed between the low and high temperatures tested. The experiments at acidic conditions below the target pH values and titrated to pH 1.5 or 3.5 using aqueous sodium hydroside solution. Measurements of solubilized concentration were those from samples analyzed after 24 hours of time to equilibrate.

Example 5

An indexing approach was used to model and determine a surprising cyclodextran ("CD"):carfilzomib ("CFZ") complexation ratio.

[1] Phase Solubility Study

SBE-β-CD was dissolved in WFI to achieve different CD % concentrations.

Excess CFZ-API solids were charged to the SBE-β-CD solution and homogenized for 1 hour via a probe style high-shear mixer to disperse API agglomerates prior their subsequent dissolution.

The slurry pH was lowered using acid to initiate solubilization and thereby complexation. Overhead mixing with a marine style impeller was continued for up 48 hours. The was adjusted upward to pH 3.5 with $NaOH_{(aq)}$.

Total dissolved CFZ as a function of SBE-β-CD concentration was determined via sampling, filtration and HPLC analysis.

[2] Compounding Study

SBE-β-CD was dissolved in WFI to achieve 25% (w/v) solution. A suspension of CFZ-API in the SBE-β-CD solution was prepared by homogenization per the solubility study API solids were added in all experiments to theoretically yield a ~6 mg/mL final solution to mimic the commercial process After homogenization, pH was lowered using citric acids to affect solubilization, while continuing mixing up 24 hours. Then, all preparations were adjusted to pH 3.5. Dissolved concentration as a function of time was measured by sampling, filtration, then HPLC analysis to monitor the kinetics of complexation in the slurry based process.

[3] Results (Phase Solubility)

Figure 7:
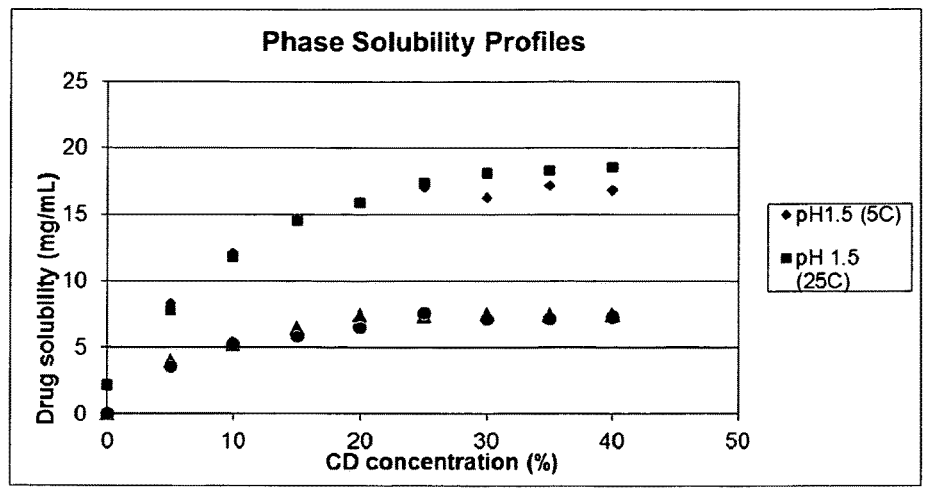
FIG. 7 is a graph that illustrates that the aqueous solubility of carfilzomib increased as a function of SBE-β-CD concentration. The concave-down phase solubility profile can be classified as An-type complexation behavior. Starting with low pH has a significant solubility enhancement, whereas temperature has negligible effect. See Example 5.

The phase solubility diagram (FIG. 7) shows that the aqueous solubility of CFZ increased as a function of SBE-β-CD concentration. The concave-down phase solubility profile can be classified as An-type complexation behavior. Starting with low pH has a significant solubility enhancement, whereas temperature has negligible effect.

[4] Results (Compounding Study)

Figure 8:
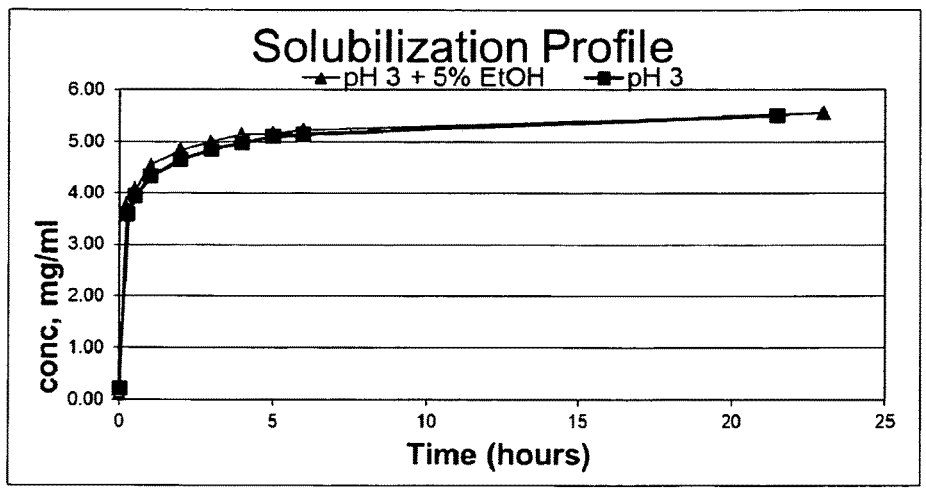
FIG. 8 is a graph that illustrates the solubilization data for carfilzomib during compounding as a function of time at pH values 1.5 and 3 (at 5° C.), as well as for 5% ethanol. See Example 5.

FIG. 8 shows the solubilization data of CFZ during compounding as a function of time at pH values 1.5 and 3 (at 5° C.), as well as for 5% ethanol.

Very fast solubilization was observed when compounding started with lowest pH

Solubilization during compounding and pH 3 showed a similarly rapid initial rate, which then slows remarkably and does not reaching equilibrium by 24 hours Addition of ethanol at pH 3 did not impact solubilization behavior, which indicates micelle formation is unlikely a rate limiting step for this system.

[5] Model Selection and Interpretation

A first order mass transfer dissolution model ("The approach to solubility equilibrium in crystallizing and dissolving systems." Dalziel, S. M.; White, E. T. & Johns, M. R. 2002 *Dev. Chem. Eng. Mineral Process* 10(5/6) 521-537) was a poor fit to time course data, indicating that the rate of overall solubilization is largely governed by a slower rate mechanism than dissolution.

Micellar intermediate states were considered unlikely to be rate governing since time course complexation experiments in 5% aqueous ethanol were not substantially different in overall rates.

The Law of Mass Action was applied, as given by equation (1), with equilibrium state described by equation (3). Hence the driving force for complexation in the non-dissolution limited state (equation 4) is the extent to which the system is away from equilibrium, and the overall kinetic rate becomes proportional to free cyclodextrin raised to the power x, which corresponds to its complexed stoichiometric ratio with the API.

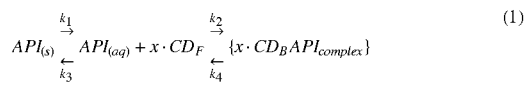

$$CD_T = CD_F + CD_B \quad (2a)$$

$$C_T = API_{(dissolved)} + API_{(complexed)} \quad (2b)$$

$$K_{stab} = \frac{[\{x \cdot CD_B API_{complex}\}]^1}{[API_{(aq)}]^1 \cdot [CD_F]^x} \quad (3)$$

Driving Force for complexation = $(K_{stab} - K_t)$ (4)

If dissolution is not rate limiting, intrinsic solubility is small, and no other intermediate state, then complexation rate= $(k_2-k_4)$ $$C_T \cong [CD_F]^x \quad (5)$$

At the boundary condition of $CD_T=0$, $C_T$=intrinsic solubility of CFZ at the given pH and temperature.

Plotting $C_T$ on Y-axis and $CD_F$ on X-axis in Molar units should converge to a linear relationship if the X-axis is transformed to the power of 1/x. Solving for x provides the stoichiometry of complexation $API_{(s)}$ active pharmaceutical ingredient, solid phase
$API_{(aq)}$ active pharmaceutical ingredient, dissolved phase
$CD_F$ cyclodextrin, free (uncomplexed)
$CD_B$ cyclodextrin, bound (complexed)
$CD_T$ cyclodextrin, total
x stoichiometric coefficient
$k_n$ reaction rate constants
$K_{stab}$ Complexation equilibrium stability constant
$K_t$ Complexation reaction coordinate and time t Experimental Data and Modeling:

Time course data for observed API concentration for various conditions such as CD %, pH, mixing speed, temperature.

Multiple coordinates for $CD_T$, and solubilized API (total: dissolved and complexed)

[6] Transformation of Experimental Data

Cyclodextrin and observed carfilzomib concentrations were converted to molar units.

Intrinsic solubility of carfilzomib was small and maintained as a constant in the analysis rather than being corrected, due to precision limitations (equation 2b).

Free and Bound concentrations of cyclodextrin were calculated from equation (2a), assuming multiple scenarios of complexation stoichiometries (x:1).

Figure 9:
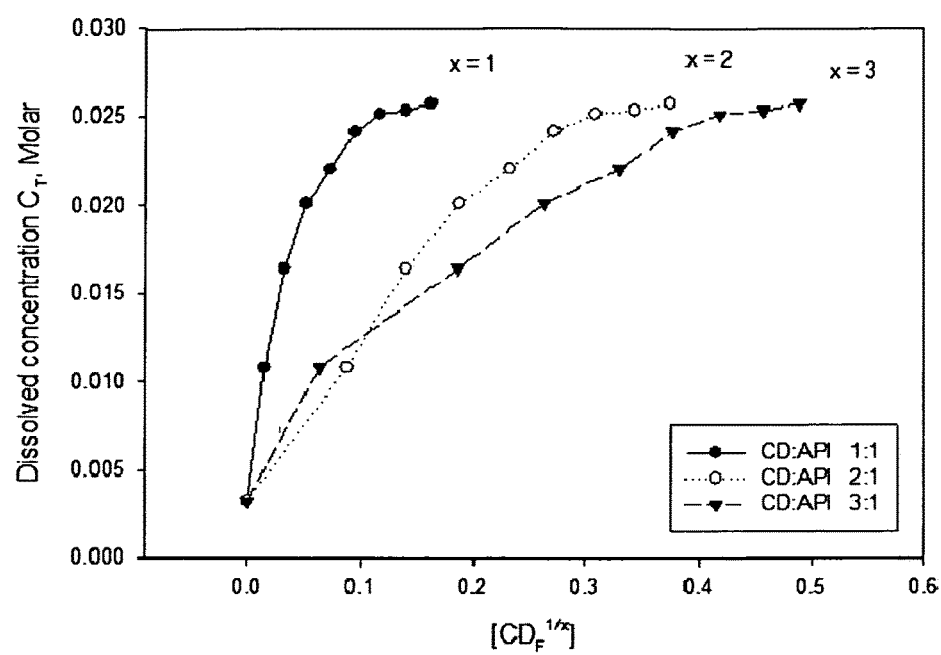
FIG. 9 is a graph that illustrates molar solubilized carfilzomib versus complexation indexed free cyclodextrin.

A plot was generated displaying observed solubilization as a function of free cyclodextrin ($CD_F$), indexed to the inverse of its complexation stoichiometry (1/x). The transformed data was evaluated to show where the plot approaches linearity (excluding the intrinsic solubility value). This was approximately x=2-3. See FIG. 9.

[7] Conclusions

The aqueous solubility of CFZ increased as a function of SBE-β-CD concentration. The phase solubility profile can be classified as An-type.

A stoichiometric ratio of 2 or 3 cyclodextrins per API molecule in the complexed state was observed for CFZ with SBE-β-CD.

The poor fit of a first order mass transfer dissolution model to this data, and the lack of significant change to the observed complexation rate in aqueous ethanolic solution (Self-assembled cyclodextrin aggregates and nanoparticles. Messner M., Jansook P., Kurkov S V and Loftsson Int J Pharm. 2010 Mar. 15; 387(1-2):199-208) suggested that neither dissolution nor micelle formation are the rate limiting step. More likely the overall process rate is governed by the rate of complexation ($k_2$). This implies that API physical properties such as particle size and surface area, as well as process variables such as mixer design and operation (which influence $k_1$) may not be critical to process performance and robustness. Commercial process design space and validation studies verified this.

A power law relationship of complexation rate to free cyclodextrin concentration raised to the stoichiometric exponent correlates to the observed kinetic behavior: initially fast (0→4.5 mg/mL first 2 hours), then very slow to equilibrate (4.5→5.5 mg/mL in >20 hours).

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for preparing a low chloride pharmaceutical composition for use in treating multiple myeloma, the method comprising:
    (i) providing a first combination comprising:
        (a) a compound having a structure:

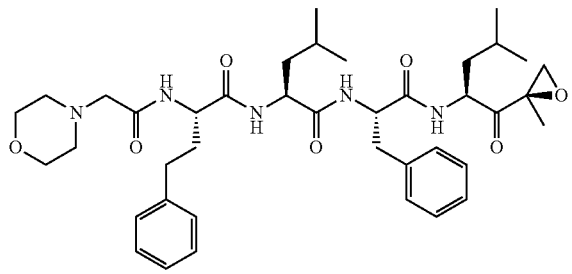 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof;
        (b) a low chloride sulfobutyl ether beta cyclodextrin ("SBECD"); and
        (c) water;
    wherein the low chloride SBECD has a chloride ion content of 0.05% w/w or less and the first combination is heterogeneous and the compound or salt has a low solubility in the first combination; and
        (ii) contacting the first combination with a non-chloride acid to form a second combination, wherein the compound is more soluble in the second combination than in the first combination.

2. The method of claim 1, wherein the first combination comprises less than 0.5% w/v of organic solvent or buffer.

3. The method of claim 1, wherein the second combination comprises a complex of the compound and the SBECD.

4. The method of claim 1, wherein the acid is added in the form of an aqueous solution.

SEQUENCE LISTING

```
<160> NUMBER OF SEQ ID NOS: 2

<210> SEQ ID NO 1
<211> LENGTH: 10
<212> TYPE: PRT
<213> ORGANISM: Rattus Rattus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Xaa Gln Asn Pro Met Xaa Tyr Gly Tyr Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Arg Ala Ala Leu Gly Asn Ile Ser Glu Asn
1               5                   10
```

5. The method of claim 1, wherein the mole ratio of chloride ion to compound in the first combination is not more than 0.32.

6. The method of claim 1, wherein providing a first combination (step (i)) comprises adding the compound to a solution of the low chloride SBECD and the water.

7. The method of claim 6, wherein the compound is a crystalline form of the compound and has an X-ray powder diffraction pattern comprising 2 to 8 characteristic peaks expressed in degrees 2θ at 6.10, 9.32, 10.10, 12.14, 13.94, 18.44, 20.38, and 23.30.

8. The method of claim 1, wherein the first combination is a slurry or suspension and the method further comprises mixing the first combination, as a slurry or suspension, prior to contacting the first combination with an acid.

9. The method of claim 1, wherein the method further comprises mixing the second combination for a time sufficient to achieve a homogeneous third combination.

10. The method of claim 9, wherein the concentration of the compound in the third combination is from 1 mg/mL to 20 mg/mL.

11. The method of claim 9, wherein the pH of the third combination is from 2 to 4.

12. The method of claim 9, wherein the method further comprises filtering the third combination.

13. The method of claim 9, wherein the method further comprises lyophilizing the third combination to provide a lyophilizate.

14. The method of claim 13, wherein the method further comprises mixing the lyophilizate with sterile water for injection.

15. The method of claim 14, further comprising mixing the lyophilizate with citric acid.

16. A method for preparing a low chloride pharmaceutical composition, the method comprising:
 (i) providing a first combination comprising:
  (a) a compound having a structure:

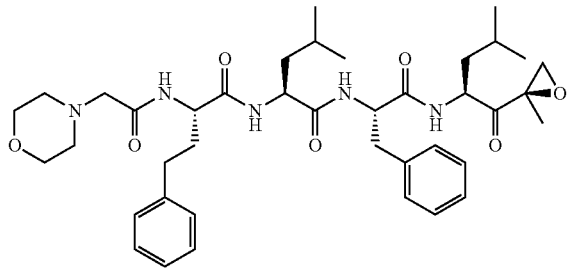 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof;
  (b) low chloride SBECD; and
  (c) water for injection;
 wherein the low chloride SBECD has a chloride ion content of 0.05% w/w or less and the first combination is heterogeneous and the compound or salt has a low solubility in the first combination; and (ii) contacting the first combination with an aqueous solution of citric acid to form a second combination, wherein the compound is more soluble in the second combination than in the first combination.

17. The method of claim 16, wherein the first combination comprises less than 0.5% w/v of organic solvent or buffer.

18. The method of claim 16, wherein the second combination comprises a complex of the compound and the low chloride SBECD.

19. The method of claim 16, wherein the mole ratio of chloride ion to compound in the first combination is not more than 0.32.

20. The method of claim 16, wherein step (i) comprises adding the compound to a solution of the low chloride SBECD and the water.

21. The method of claim 20, wherein the compound is a crystalline form of the compound and has an X-ray powder diffraction pattern comprising 2 to 8 characteristic peaks expressed in degrees 2θ at 6.10, 9.32, 10.10, 12.14, 13.94, 18.44, 20.38, and 23.30.

22. The method of claim 16, wherein the method further comprises mixing the first combination prior to contacting the first combination with an acid.

23. The method of claim 16, wherein the method further comprises mixing the second combination for a time sufficient to achieve a homogeneous third combination.

24. The method of claim 23, wherein the concentration of the compound in the third combination is from 1 mg/mL to 20 mg/mL.

25. The method of claim 23, wherein the pH of the third combination is from 2 to 4.

26. The method of claim 23, wherein the method further comprises filtering the third combination.

27. The method of claim 23, wherein the method further comprises lyophilizing the third combination to provide a lyophilizate.

28. The method of claim 27, wherein the method further comprises mixing the lyophilizate with sterile water for injection.

29. The method of claim 28, further comprising mixing the lyophilizate with citric acid.

30. The method of claim 4, wherein the acid is citric acid.

* * * * *

UNITED STATES PATENT AND TRADEMARK OFFICE
CERTIFICATE OF CORRECTION

PATENT NO. : 10,159,746 B2
APPLICATION NO. : 14/399582
DATED : December 25, 2018
INVENTOR(S) : Evan Lewis et al.

Page 1 of 2

It is certified that error appears in the above-identified patent and that said Letters Patent is hereby corrected as shown below:

In the Specification

At Column 8, Line 20, "one more" should be -- one or more --.

At Column 13, Lines 24-25, "(5-0H-trp)," should be -- (5-OH-trp), --.

At Column 13, Line 31, "(H$_2$P0$_3$-Tyr)," should be -- (H$_2$PO$_3$-Tyr), --.

At Column 13, Line 39, ""L" or "1"" should be -- "L" or "l" --.

At Column 14, Line 47, "I," should be -- 1, --.

At Column 18, Line 10, "C$_{1-6}$alkyl," should be -- C$_{1-6}$aralkyl, --.

At Column 18, Line 57, "(R$^{10}$)$_3$N$^+$(CH$_2$)n-," should be -- (R$^{10}$)$_3$N$^+$(CH$_2$)n—, --.

At Column 20, Line 34, "preferably 0;" should be -- preferably O; --.

At Column 23, Line 30, "one ore" should be -- one or --.

At Column 23, Line 51, "an to intermolecular" should be -- an intermolecular --.

At Column 29, Line 13, "acid, is" should be -- acid is --.

At Column 31, Line 34, "e.g.," should be -- (e.g., --.

At Column 37, Line 7, "comprises up" should be -- comprises up to --.

At Column 41, Line 2, "lymphoplamacytic" should be -- lymphoplasmacytic --.

Signed and Sealed this
Nineteenth Day of January, 2021

Andrei Iancu
*Director of the United States Patent and Trademark Office*

CERTIFICATE OF CORRECTION (continued)
U.S. Pat. No. 10,159,746 B2

At Column 42, Line 32, "NF-kB" should be -- NF-κB --.

At Column 46, Line 41, "x gene," should be -- κ gene, --.

At Column 61, Line 64, "(target pH 3.5)" should be -- (target pH 3.5)) --.

At Column 67, Line 28, "for up 48 hours. The" should be -- for up to 48 hours. This --.

At Column 68, Line 32, "$C_T \geq [CD_F]^x$" should be -- $C_T \propto [CD_F]^x$ --.

At Column 69, Line 12, "Kurkov S V" should be -- Kurkov SV --.